(12) United States Patent
Chen et al.

(10) Patent No.: US 11,666,779 B2
(45) Date of Patent: Jun. 6, 2023

(54) SHIELDING APPARATUS

(71) Applicant: OUR UNITED CORPORATION, Xi'an (CN)

(72) Inventors: Fangzheng Chen, Xi'an (CN); Daliang Li, Xi'an (CN)

(73) Assignee: Our United Corporation

( * ) Notice: Subject to any disclaimer, the term of this patent is extended or adjusted under 35 U.S.C. 154(b) by 0 days.

(21) Appl. No.: 17/110,727

(22) Filed: Dec. 3, 2020

(65) Prior Publication Data

US 2021/0330990 A1    Oct. 28, 2021

Related U.S. Application Data

(63) Continuation of application No. PCT/CN2020/087089, filed on Apr. 26, 2020.

(51) Int. Cl.
*A61N 5/10* (2006.01)
*G21F 7/00* (2006.01)
*A61G 10/00* (2006.01)

(52) U.S. Cl.
CPC ............... *A61N 5/10* (2013.01); *A61G 10/00* (2013.01); *G21F 7/00* (2013.01); *A61N 2005/1094* (2013.01)

(58) Field of Classification Search
CPC .. A61N 5/00; A61N 2005/1094; A61G 10/00; A61G 10/005; G21F 7/00; G21F 7/005
See application file for complete search history.

(56) References Cited

U.S. PATENT DOCUMENTS

| 6,325,538 | B1 | 12/2001 | Heesch | |
|---|---|---|---|---|
| 6,653,648 | B2* | 11/2003 | Goldstein | A61B 6/107 250/515.1 |
| 2007/0269008 | A1* | 11/2007 | Pomper | A61G 3/001 378/65 |
| 2009/0110152 | A1* | 4/2009 | Manzke | A61B 6/4423 378/195 |
| 2015/0328432 | A1* | 11/2015 | Liu | A61M 21/0094 600/27 |
| 2016/0095558 | A1* | 4/2016 | Choy | A61N 5/1081 600/407 |

(Continued)

FOREIGN PATENT DOCUMENTS

| CN | 101312691 | 11/2008 |
|---|---|---|
| CN | 201157365 | 12/2008 |

(Continued)

*Primary Examiner* — Samuel G Gilbert
(74) *Attorney, Agent, or Firm* — Emerson, Thomson & Bennett, LLC; Roger D. Emerson; Peter R. Detorre

(57) ABSTRACT

A shielding apparatus is provided. The shielding apparatus includes: at least one shielding shell segment, the at least one shielding shell segment constituting a shielding chamber, the shielding chamber being arranged on a periphery of a radiation device and shielding radiation generated by the radiation device. The shielding chamber is arranged on the periphery of the radiation device, and the shielding chamber at least partially shields scattering radiation generated by the radiation device, which can thus reduce the requirements of the radiation device for radiation shielding of a dedicated machine room or get rid of the dependence of the radiotherapy device on a dedicated machine room.

17 Claims, 19 Drawing Sheets

(56) References Cited

U.S. PATENT DOCUMENTS

2017/0294244 A1* 10/2017 Benson ................... G21F 5/04
2018/0280733 A1* 10/2018 Weidlich .............. A61B 6/4078
2019/0069856 A1     3/2019 Achkire et al.

FOREIGN PATENT DOCUMENTS

CN          106823161        6/2017
WO      WO2007060561         5/2007
WO      WO2015161036        10/2015

* cited by examiner

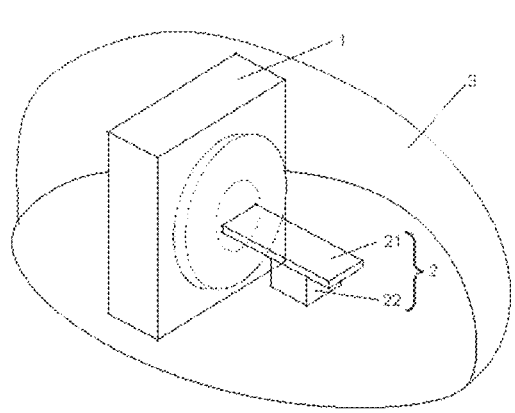
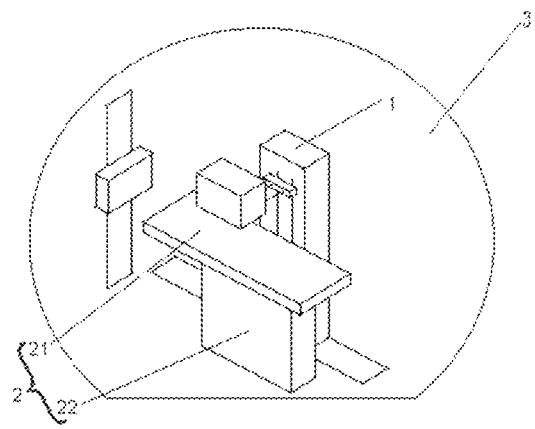
Fig. 3e
Fig. 3f
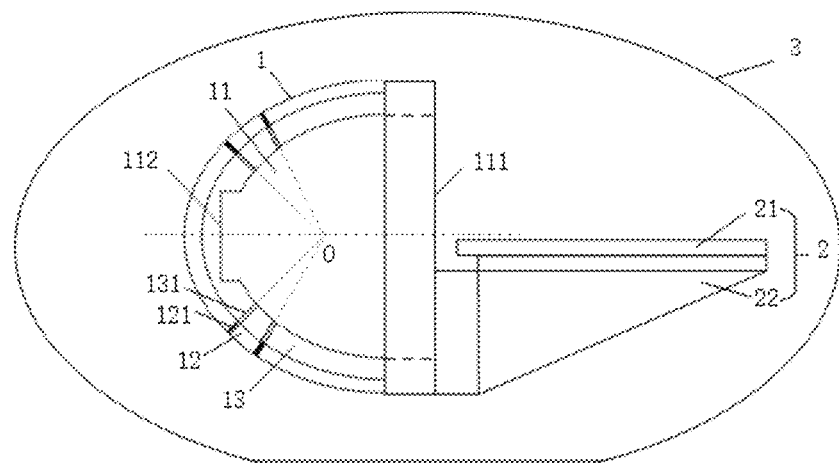
Fig. 3g
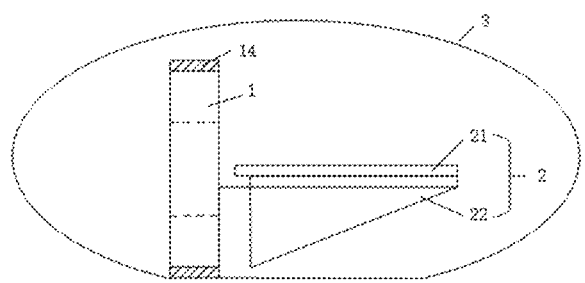
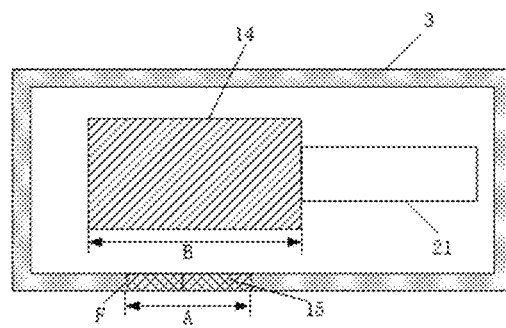
Fig. 4
Fig. 5

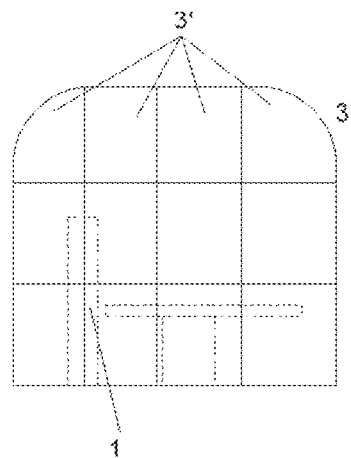
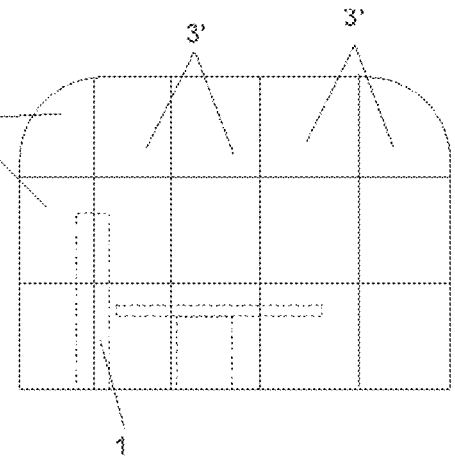
Fig. 11c  Fig. 11d
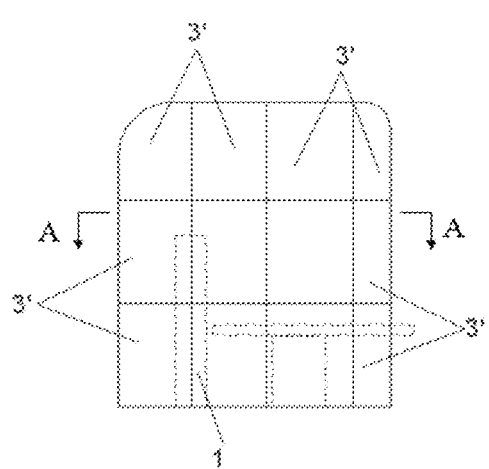
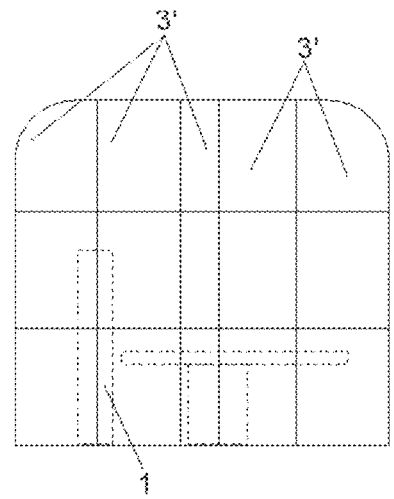
Fig. 11e  Fig. 11f
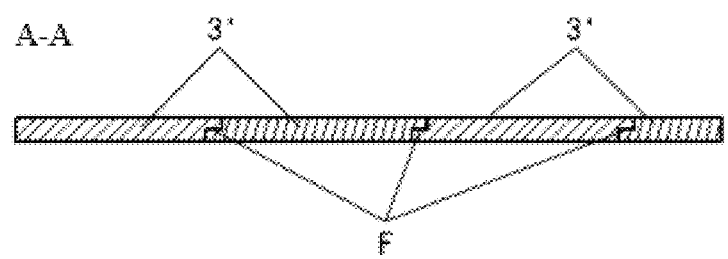
Fig. 12

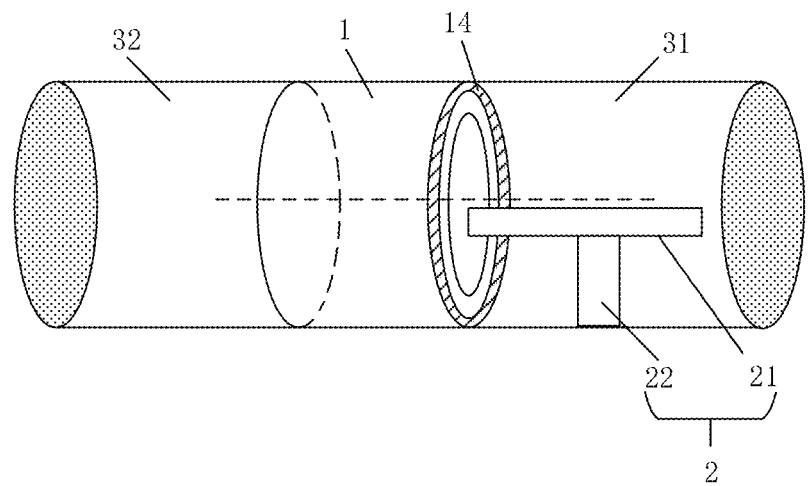
Fig. 18
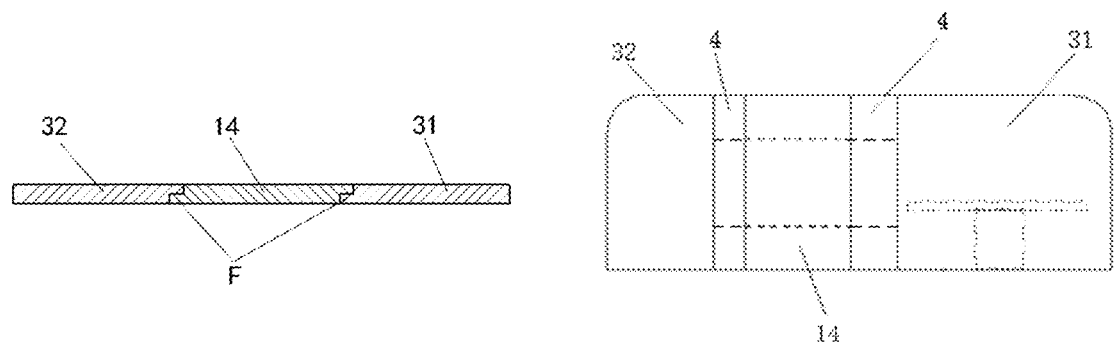
Fig. 19
Fig. 20
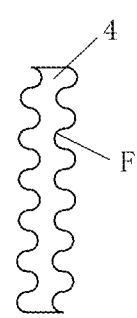
Fig. 21
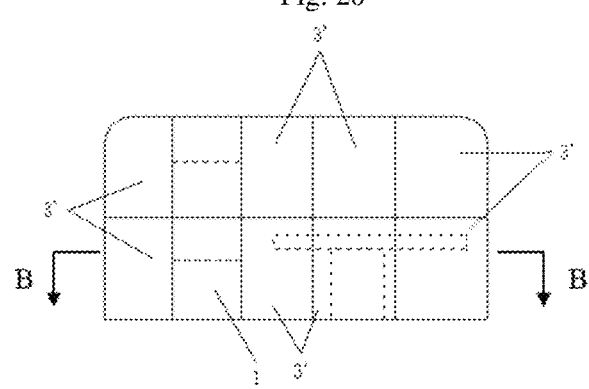
Fig. 22

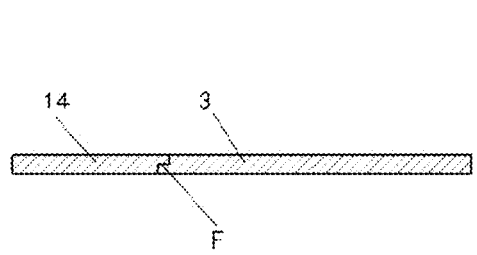
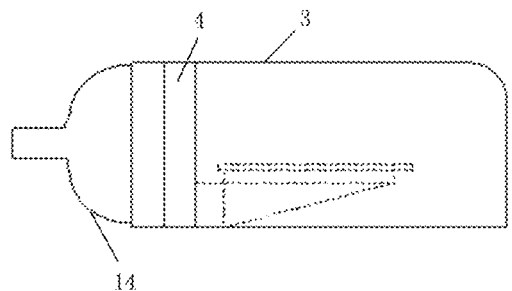
Fig. 31　　　　　　　　Fig. 32
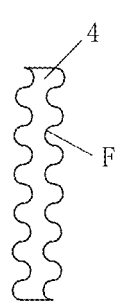
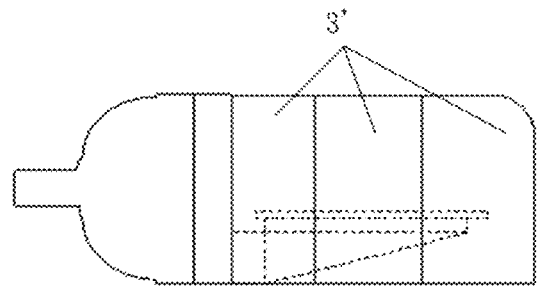
Fig. 33　　　　　　　　Fig. 34
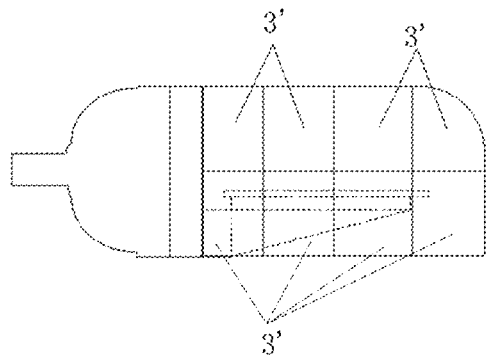
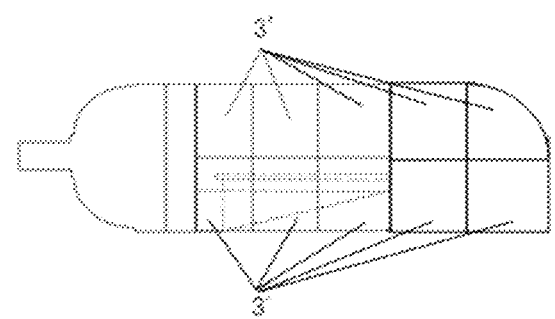
Fig. 35a　　　　　　　　Fig. 35b
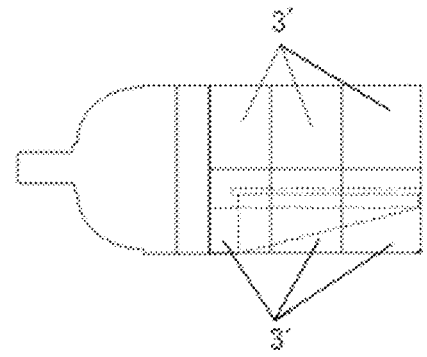
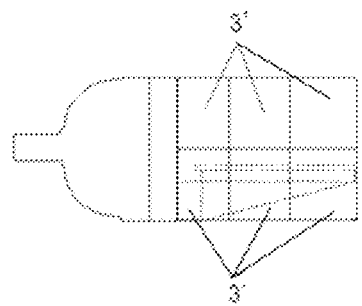
Fig. 35c　　　　　　　　Fig. 35d

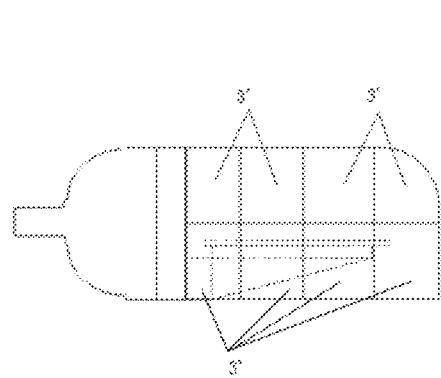
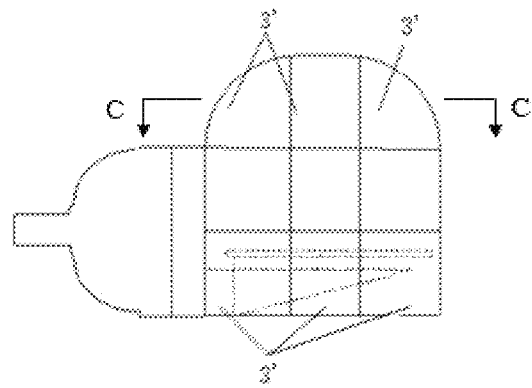
Fig. 35e       Fig. 35f
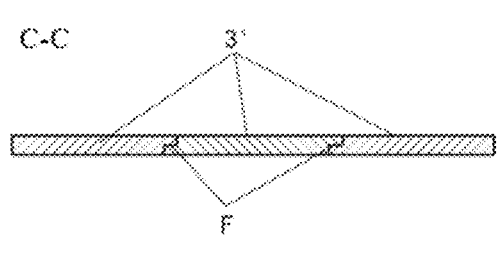
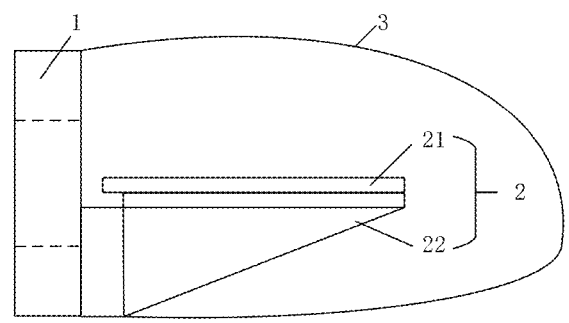
Fig. 36       Fig. 37
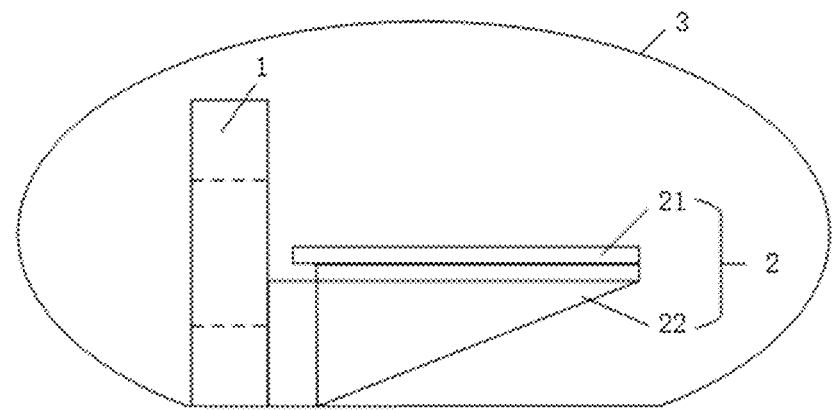
Fig. 38

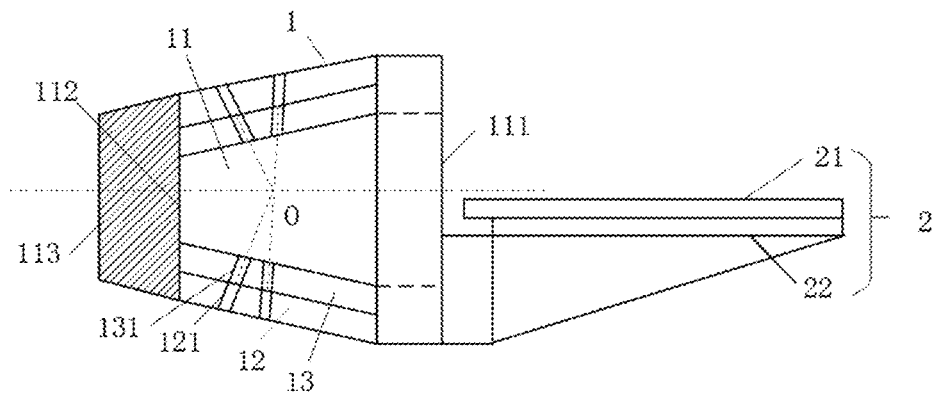
Fig. 43
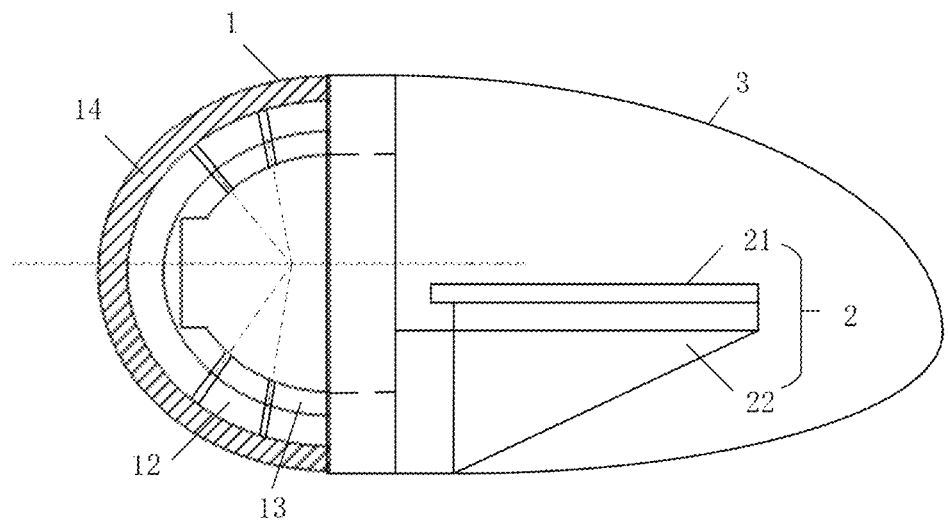
Fig. 44
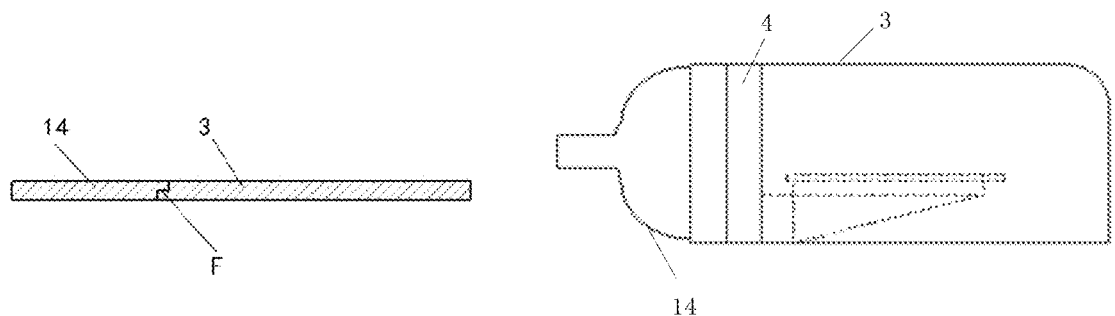
Fig. 45
Fig. 46

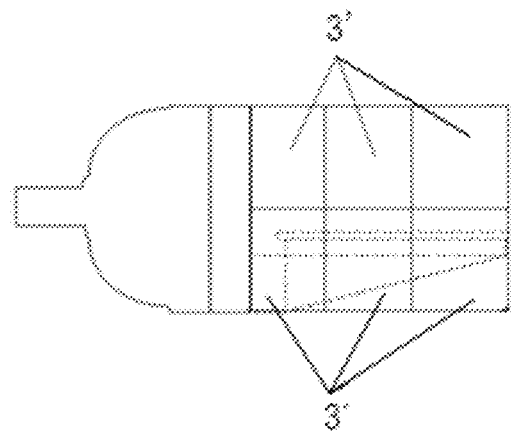
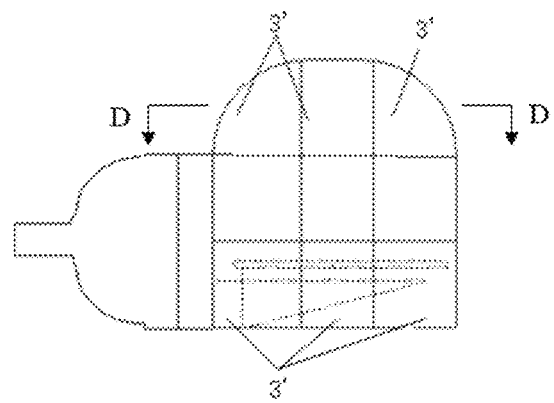
Fig. 49e　　　　　　　　　　　Fig. 49f
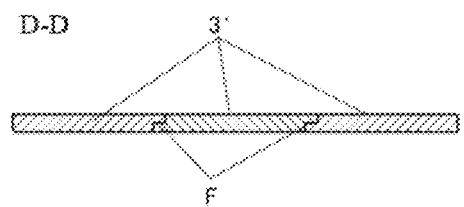
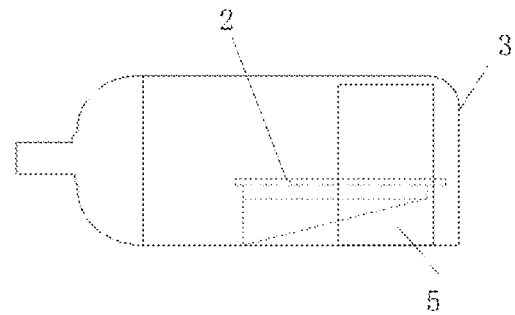
Fig. 50　　　　　　　　　　　Fig. 51
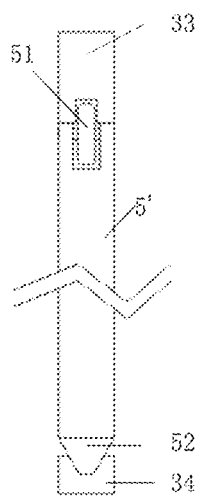
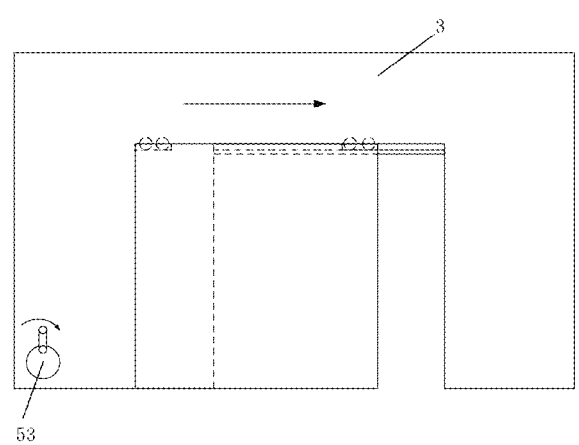
Fig. 52a　　　　　　　　　　　Fig. 52b

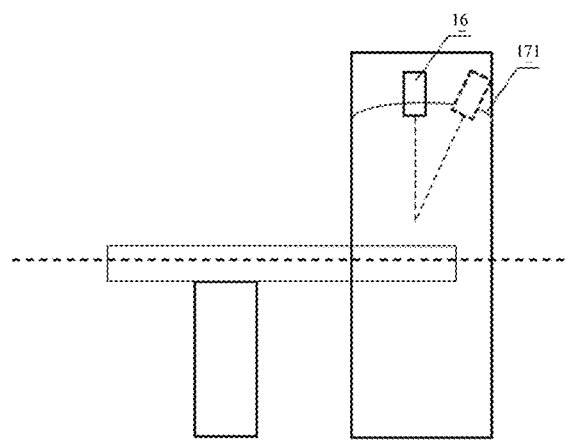
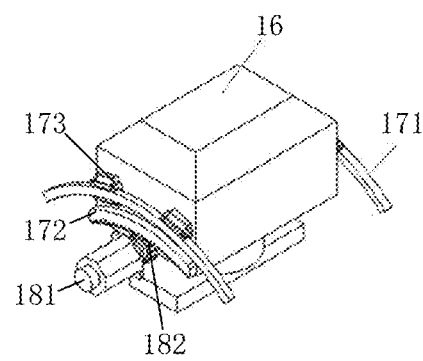
Fig. 59    Fig. 60
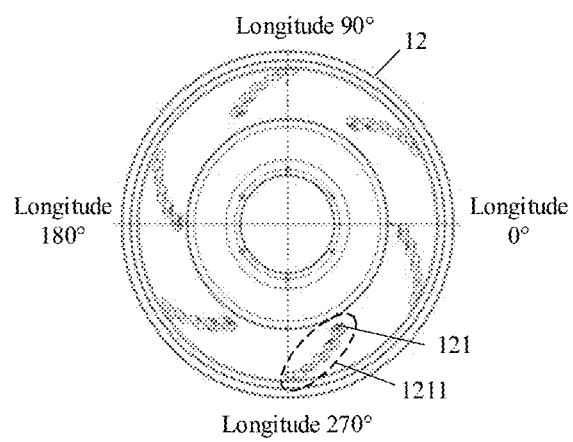
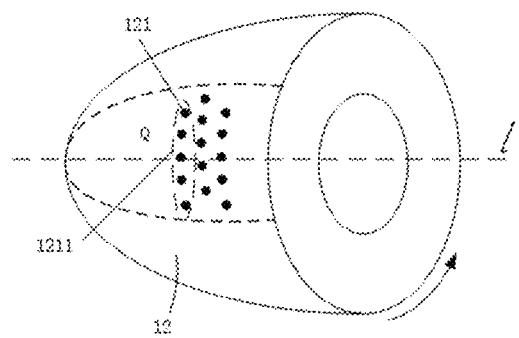
Fig. 61    Fig. 62
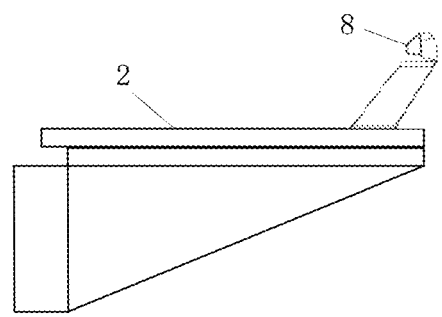
Fig. 63

SHIELDING APPARATUS

CROSS-REFERENCE TO RELATED APPLICATION

The present disclosure is a continuation of international application No. PCT/CN2020/087089 filed on Apr. 26, 2020, which is hereby incorporated by reference in its entirety.

TECHNICAL FIELD

The present disclosure relates to the field of medical technology, particularly to a shielding apparatus.

BACKGROUND

With the development of medical technology, radiation therapy has become an important means in medical diagnosis and treatment. A radiation source emits radiation, and the radiation passes through a human body from different angles to diagnose and treat the patient. Because radiation diagnosis or therapy devices are radioactive, the radiation will harm operators or other people during diagnosis and treatment. Therefore, in the existing facilities for placing radiation devices, houses for accommodating the radiation devices need to be renovated, in order to provide sufficient radiation shielding to ensure no harm to the operators or other people.

SUMMARY

In view of this, one of the technical problems to be solved by the embodiments of the present disclosure is to provide a shielding apparatus for overcoming at least some of the problems in the prior art.

An embodiment of the present disclosure provides a shielding apparatus, the shielding apparatus including: at least one shielding shell segment, the at least one shielding shell segment constituting a shielding chamber, the shielding chamber being arranged on the periphery of a radiation device and radiation generated by the radiation device is shielded by the shielding chamber.

It can be seen from the above embodiment that the shielding chamber can be arranged on the periphery of the radiation device, and the shielding chamber at least partially shields the scattered radiation generated by the radiation device, which can thus reduce the requirements for radiation shielding of a dedicated machine room or get rid of the dependence of a radiotherapy device on a dedicated machine room.

BRIEF DESCRIPTION OF THE DRAWINGS

To describe the technical solutions in the embodiments of the present disclosure or in the prior art more clearly, the following briefly introduces the accompanying drawings required for describing the embodiments or the prior art. Apparently, the accompanying drawings in the following description show only some of the embodiments of the present disclosure, and a person of ordinary skill in the art may still derive other drawings from these accompanying drawings.

FIGS. 3a-3g are schematic structural diagrams of a radiotherapy device with a closed shielding chamber according to an embodiment of the present disclosure;

FIG. 4 is a schematic diagram of another radiotherapy device according to an embodiment of the present disclosure;

FIG. 5 is a top view of FIG. 4;

FIGS. 11a-11f are schematic diagrams of the shielding chamber formed by splicing different shielding shell segments according to an embodiment of the present disclosure;

FIG. 12 is a schematic cross sectional view of a plurality of spliced shielding shell segments taken along the line A-A of FIG. 11e according to an embodiment of the present disclosure;

FIG. 18 is a schematic diagram of still another radiotherapy device according to an embodiment of the present disclosure;

FIG. 19 is a schematic diagram of coupling between a shielding chamber and a shielding layer by an adapting structure according to an embodiment of the present disclosure;

FIG. 20 is a schematic diagram of coupling between the shielding chamber and the shielding layer by an intermediate connector according to an embodiment of the present disclosure;

FIG. 21 is a schematic structural diagram of the intermediate connector according to an embodiment of the present disclosure;

FIG. 22 is a schematic structural diagram of the shielding chamber formed by splicing shielding shell segments according to an embodiment of the present disclosure;

FIG. 31 is a schematic diagram of coupling between a shielding chamber and a shielding layer by an adapting structure according to an embodiment of the present disclosure;

FIG. 32 is a schematic diagram of coupling between the shielding chamber and the shielding layer by an intermediate connector according to an embodiment of the present disclosure;

FIG. 33 is a schematic structural diagram of the intermediate connector according to an embodiment of the present disclosure;

FIG. 34 is a schematic structural diagram of the shielding chamber formed by splicing shielding shell segments according to an embodiment of the present disclosure;

FIGS. 35a-35f are schematic diagrams of the shielding chamber formed by splicing different shielding shell segments according to an embodiment of the present disclosure;

FIG. 36 is a schematic cross sectional view of a plurality of spliced shielding shell segments taken along the line C-C of FIG. 35f according to an embodiment of the present disclosure;

FIG. 37 is a schematic structural diagram of a radiotherapy device according to an embodiment of the present disclosure;

FIG. 38 is a schematic diagram of another radiotherapy device according to an embodiment of the present disclosure;

FIG. 43 is a schematic structural diagram of another gantry of a radiotherapy device according to an embodiment of the present disclosure;

FIG. 44 is a schematic diagram of still another radiotherapy device according to an embodiment of the present disclosure;

FIG. 45 is a schematic diagram of coupling between a shielding chamber and a shielding layer by an adapting structure according to an embodiment of the present disclosure;

FIG. 46 is a schematic structural diagram of coupling between the shielding chamber and the shielding layer by an intermediate connector according to an embodiment of the present disclosure;

FIGS. 49a-49f are schematic diagrams of the shielding chamber formed by splicing different shielding shell segments according to an embodiment of the present disclosure;

FIG. 50 is a schematic cross sectional view of a plurality of spliced shielding shell segments taken along the line D-D of FIG. 49f according to an embodiment of the present disclosure;

FIG. 51 is a schematic diagram of a patient entrance according to an embodiment of the present disclosure;

FIGS. 52a-52b are schematic diagrams of a suspended roller structure according to an embodiment of the present disclosure;

FIG. 59 is a schematic structural diagram of movement of a treatment head along a curved guide rail according to an embodiment of the present disclosure;

FIG. 60 is a schematic structural diagram of cooperative movement between the treatment head and the curved guide rail according to an embodiment of the present disclosure;

FIG. 61 is a schematic structural diagram of uniform distribution of a plurality of radiation sources of a source carrier of the radiotherapy device according to an embodiment of the present disclosure;

FIG. 62 is a schematic structural diagram of concentrated arrangement of a plurality of radiation sources of a source carrier of the radiotherapy device according to an embodiment of the present disclosure;

FIG. 63 is a schematic structural diagram that an optical monitoring system is installed on a treatment couch according to an embodiment of the present disclosure;

1, gantry; 11, treatment cavity; 111, opening; 112, closed end; 113, shielding plug; 12, source carrier; 121, radiation source; 13, collimator; 131, collimating hole; 14, shielding layer; 15, entrance; 16, treatment head; 171, curved guide rail; 173, slider; 172, curved rack; 181, driving apparatus; 182, gear; 2, treatment couch; 21, mobile couch body; 23, base; 3, shielding chamber; 31, first shielding chamber; 32, second shielding chamber; 33, first recess; 34, second recess; 4, intermediate connector; 3', shielding shell segment; 5, patient entrance; 51, first top roller; 52, first bottom slide rail; 53, first hand crank; 6, operation port; 7, isolation compartment; 71, hollow cavity; 72, outer door; 73, third hand crank; 8, optical monitoring system.

DETAILED DESCRIPTION

For better understanding of the technical solutions in the embodiments of the present disclosure by those skilled in the art, the technical solutions in the embodiments of the present disclosure will be clearly and completely described with reference to the accompanying drawings in the embodiments of the present disclosure. Apparently, the described embodiments are only some of the embodiments of the present disclosure, not all of them. All other embodiments obtained by those of ordinary skill in the art based on the embodiments of the present disclosure shall fall within the protection scope of the embodiments of the present disclosure.

A radiation device, e.g., a radiotherapy device, is used in tumor treatment. Because the radiation device needs to kill tumor cells with radiation rays to treat a patient, the radiation device is often placed in a dedicated machine room with radiation shielding capability, to avoid the damage of radiation rays to the operator or other personnel, but the construction period and construction cost of the dedicated machine room limit the wide application of the radiation device.

The radiotherapy device is taken as an example below to describe the radiation device of the present disclosure, but the present disclosure is not limited thereto.

Figure 1A:
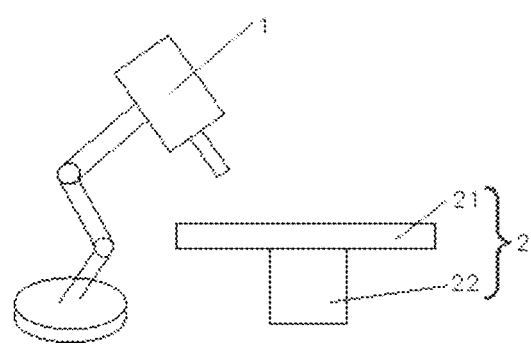
FIGS. 1a-1f are schematic structural diagrams of several radiotherapy devices.
Figure 1B:
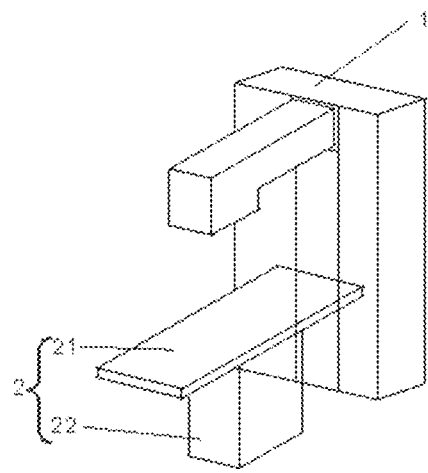
Figure 1C:
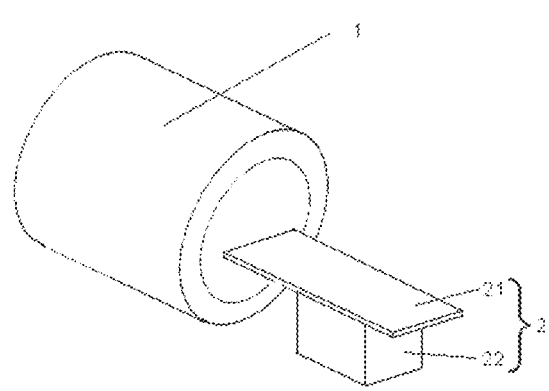
Figure 1D:
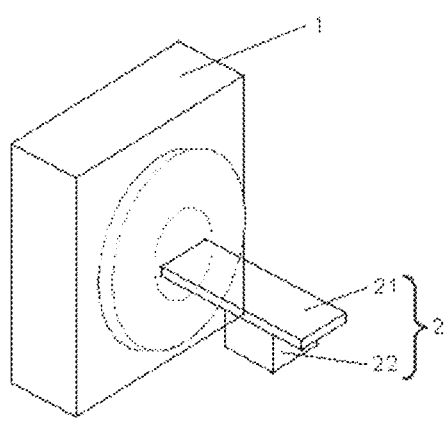
Figure 1E:
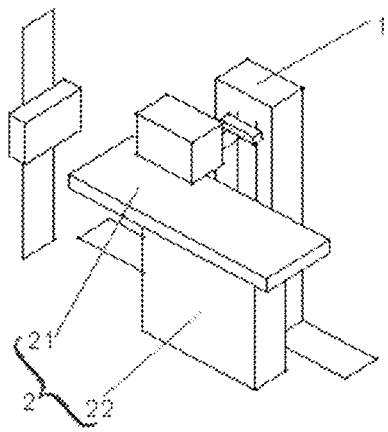
Figure 1F:
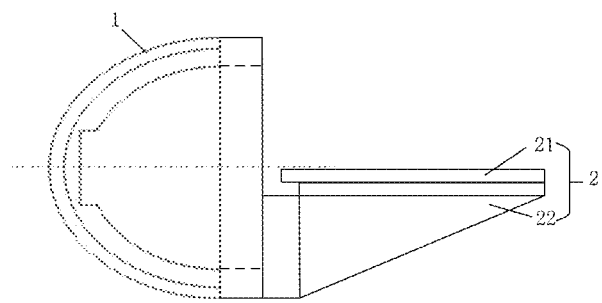
Figure 2A:
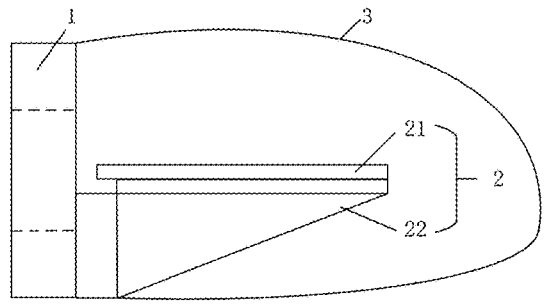
FIGS. 2a-2g are schematic structural diagrams of a radiotherapy device with a non-closed shielding chamber according to an embodiment of the present disclosure.
Figure 2B:
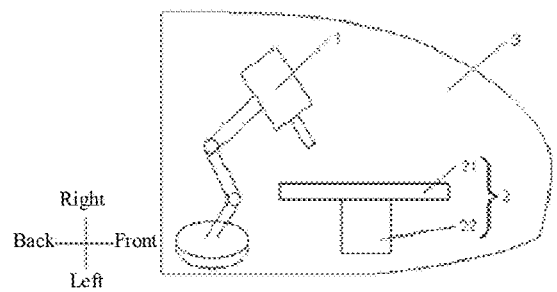
Figure 2C:
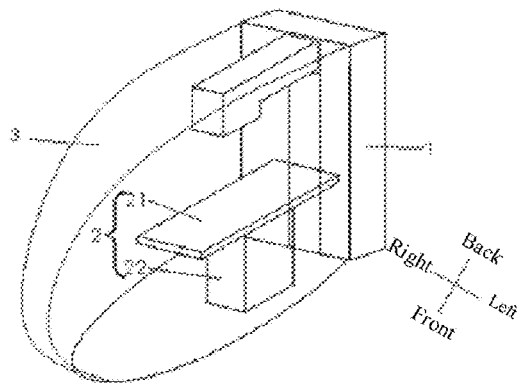
Figure 2D:
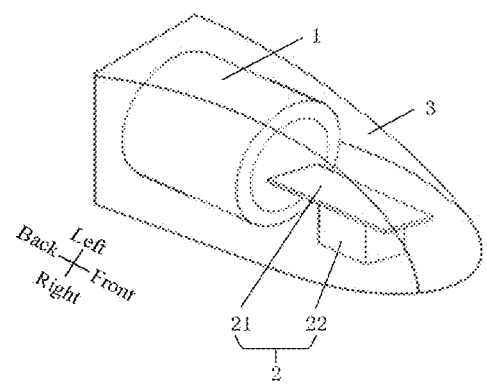
Figure 2E:
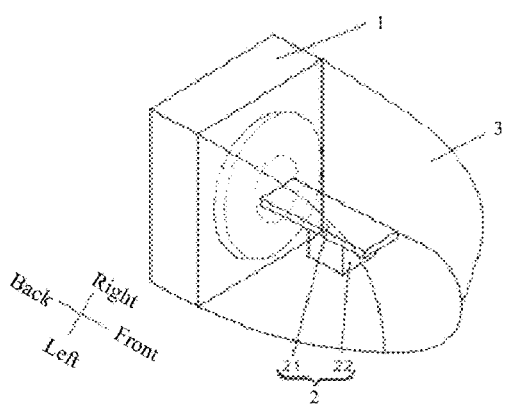
Figure 2F:
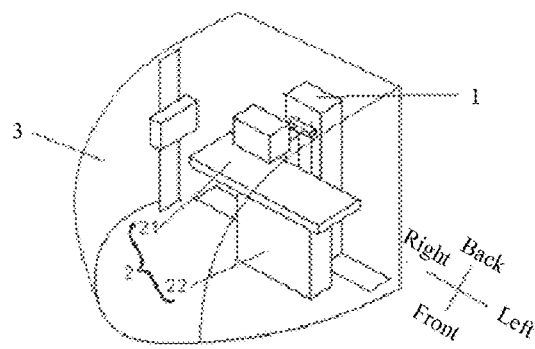
Figure 2G:
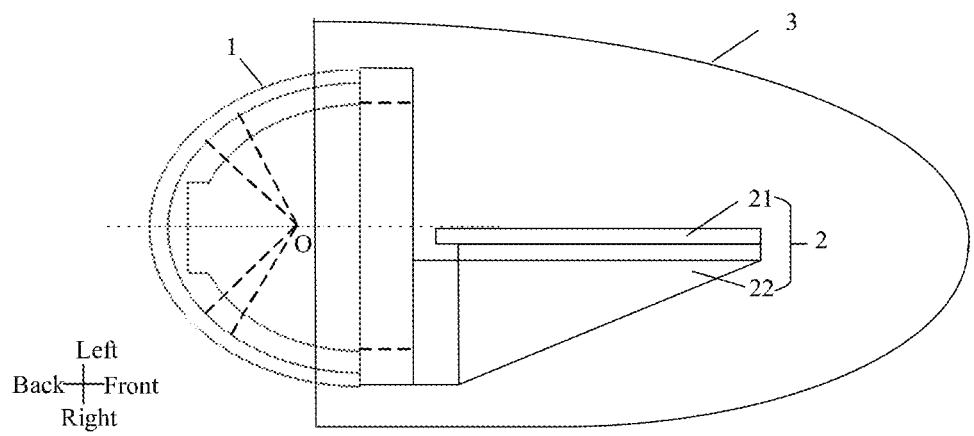
Figure 3A:
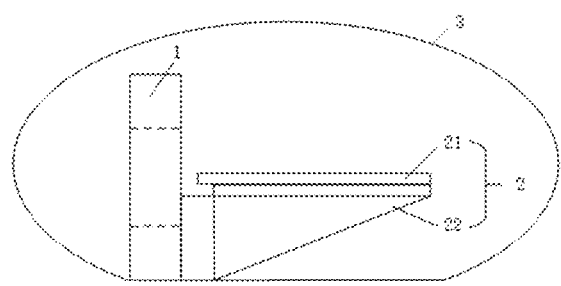
Figure 3B:
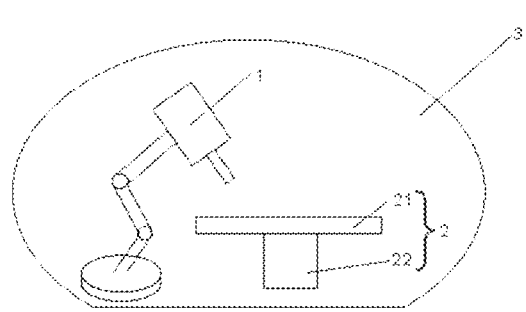
Figure 3C:
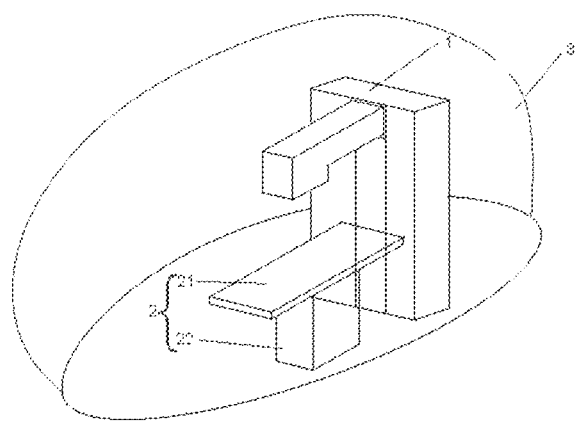
Figure 3D:
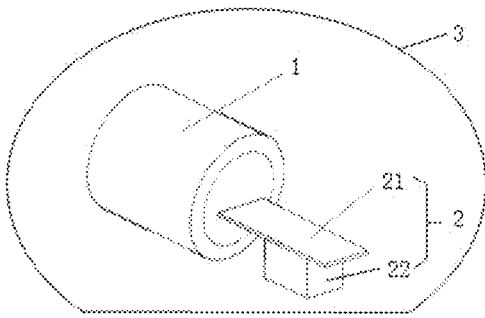

Refer to FIGS. 1*a*-1*f*, which are schematic structural diagrams of several radiotherapy devices. FIG. 1*a* is a schematic diagram of a radiotherapy device with a robotic arm gantry; FIG. 1*b* is a schematic diagram of a radiotherapy device with a C-arm gantry; FIG. 1*c* is a schematic diagram of a radiotherapy device with a cylindrical gantry; FIG. 1*d* is a schematic diagram of a CT machine; FIG. 1*e* is a schematic diagram of a DR machine; FIG. 1*f* is a schematic diagram of a radiotherapy device with a hemispherical gantry.

The radiation device generally includes a gantry 1, a radiation source (not shown in the figures) installed on the gantry 1, and a treatment couch 2 for carrying a patient. The radiation emitted by the radiation source irradiates the patient to complete diagnosis or treatment. In order to prevent physical damage of the radiation to the operator and other personnel during the diagnosis or treatment, the radiation device is usually placed in a special machine room to complete the diagnosis or treatment.

To this end, an embodiment of the present disclosure provides a shielding apparatus, including: at least one shielding shell segment, the at least one shielding shell segment constituting a shielding chamber 3, the shielding chamber 3 being arranged on the periphery of a radiation device and shielding radiation generated by the radiation device.

According to the embodiment of the present disclosure, the shielding chamber is arranged on the periphery of the radiation device, and the shielding chamber at least partially shields scattering radiation generated by the radiation device, which can thus reduce the requirements of the radiation device for radiation shielding of a dedicated machine room or get rid of the dependence of the radiation device on a dedicated machine room.

In a specific implementation of the present disclosure, the shielding chamber is a closed body or a non-closed body.

In an embodiment of the present disclosure, the treatment couch 2 includes a mobile couch body 21 and a support base 22, and the shielding chamber 3 surrounds the mobile couch body 21 and the support base 22, and is arranged on the periphery of the radiation device.

According to the embodiment of the present disclosure, the mobile couch body and the support base are surrounded within the shielding chamber, which at least shields scattering radiation of the radiation device on one side of the treatment couch, thereby reducing the requirements of the radiation device for radiation shielding of a dedicated machine room or getting rid of the dependence of the radiation device on a dedicated machine room.

In addition, since the mobile couch body and the support base of the treatment couch are both housed within the shielding chamber, the space available for the patient in the entire shielding chamber is increased, which helps to alleviate the patient's symptom of claustrophobia.

In an embodiment of the present disclosure, the shielding chamber surrounds the gantry 1 and the treatment couch 2, and is arranged on the periphery of the radiation device to form a non-closed body for shielding the radiation generated by the radiation device.

The treatment couch 2 includes a mobile couch body 21 and a support base 22.

Specifically, the shielding chamber 3 described in the embodiment of the present disclosure is housed on the periphery of the gantry 1 of the radiation device and the treatment couch 2 thereof to form a non-closed body for shielding the radiation generated by the radiation device.

As shown in FIGS. 2*a*-2*g*, the shielding chamber 3 can surround the mobile couch body 21 and the support base 22 of the treatment couch 2 and the gantry 1 from the front side (i.e. the treatment couch side), left and right sides of the radiation device, the rear side of the radiation device is open, and the shielding chamber 3 is used to shield radiation rays scattered from the front, left and right sides of the gantry.

Although the shielding chamber in the embodiment of the disclosure does not shield the radiation rays scattered from the rear side of the gantry, at least the requirements of the radiation device for the machine room are reduced. The scattering radiation of the radiation device can be shielded only by radiation shielding transformation on a wall opposite to the rear side of the radiation device, which shortens the construction period of the machine room and reduces the construction cost of the machine room.

In addition, since the mobile couch body 21 and the support base 22 of the treatment couch 2 are both housed within the shielding chamber 3, the space available for the patient in the entire shielding chamber 3 is increased, which helps to alleviate the patient's symptom of claustrophobia.

The embodiment of the present disclosure does not limit the form of the non-closed shielding chamber, and the non-closed shielding chamber may also be open on the front, right or left side, which is not limited in the embodiment of the present disclosure.

In an embodiment of the present disclosure, the shielding chamber surrounds the gantry 1 and the treatment couch 2, and is arranged on the periphery of the radiation device to form a closed body for shielding the radiation generated by the radiation device.

The treatment couch 2 includes a mobile couch body and a support base.

As shown in FIGS. 3*a*-3*g*, the shielding chamber 3 completely houses the gantry 1, the mobile couch body 21 and the support base 22, that is, the shielding chamber 3 surrounds the radiation device to form a closed body. The shielding chamber 3 can shield the radiation rays scattered from the front, left, rear, and right sides of the radiation device.

According to the embodiment of the present disclosure, the closed shielding chamber is arranged around the radiation device to form self-shielding of the radiation device, thereby eliminating the need for a dedicated machine room. The self-shielding radiation device can be placed at any position, which expands the application scenario of the radiation device.

In addition, since the mobile couch body 21 and the support base 22 of the treatment couch 2 are both housed within the shielding chamber 3, the space available for the patient in the entire shielding chamber 3 is increased, which helps to alleviate the patient's symptom of claustrophobia.

According to the embodiment of the present disclosure, a shielding layer is arranged on the outside of the gantry, the shielding chamber has at least one entrance, the entrance is a third openable shielding door, the third openable shielding door is arranged at a position of the shielding chamber opposite to the shielding layer of the gantry, and the opening size of the third openable shielding door is smaller than the size of the shielding layer of the gantry in the axial direction of the gantry.

As shown in FIGS. 4 and 5, a shielding layer 14 is arranged on the outside of the gantry 1, the shielding layer 14 has the same width as the gantry 1 in the axis direction of the gantry and is used to shield radiation rays scattered from the left, right and upper sides of the gantry 1, the shielding chamber 3 completely houses the gantry 1, the mobile couch body 21 and the support base 22, the shielding chamber 3 has an entrance 15, the entrance 15 is a third openable shielding door, the third openable shielding door is arranged on a side wall of the shielding chamber 3 and faces the shielding layer 14 of the gantry, and the opening size A of the third openable shielding door (i.e., the size of the third openable shielding door in the axial direction of the gantry) is smaller than the size B of the shielding layer 14 of the gantry in the axial direction of the gantry, so that when the third openable shielding door is opened, the radiation rays at the opening are shielded by the shielding layer 14 of the gantry, and the radiation rays in the shielding chamber 3 will not leak from the opening of the third openable shielding door.

The interface between the third openable shielding door and the shielding chamber 3 is a non-straight splicing interface to ensure that radiation rays will not leak from the interface between the shielding door and the shielding chamber. The non-straight splicing interface F may be a V-shaped surface, or a curved surface, an S surface, or a stepped surface. The embodiment of the present disclosure is not limited to the aforementioned non-straight splicing interface, and may also be implemented by other non-straight splicing interfaces.

In an embodiment of the present disclosure, the radiation device further includes a gantry configured to carry a radiation source, a shielding layer is arranged on the outside of the gantry, and the shielding chamber is coupled with the shielding layer to form a closed body or a non-closed body for shielding the radiation generated by the radiation device.

Figure 6:
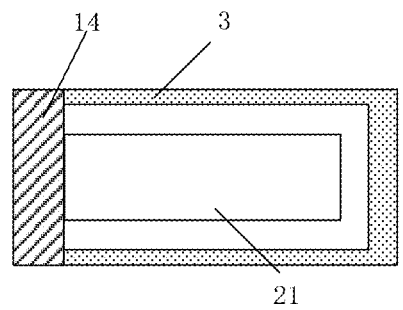
FIG. 6 is a schematic diagram of still another radiotherapy device according to an embodiment of the present disclosure.

As shown in FIG. 6, a shielding layer 14 is arranged on the outside of the gantry 1 for surrounding the gantry 1 to shield the radiation rays scattered from the left, right and upper sides of the gantry 1, the shielding chamber 3 surrounds the treatment couch 2 to house the mobile couch body 21 and the support base 22 of the treatment couch 2, and the shielding chamber 3 is coupled (directly connected or indirectly connected) with the shielding layer 14 to form a non-closed chamber, so that the rear end of the gantry is opened and the radiation rays scattered from the front, left, and right sides of the radiation device are shielded.

The embodiment of the present disclosure shields the radiation scattered from the front, left, and right sides of the gantry through the combination of the shielding chamber and the shielding layer, thereby reducing the shielding requirements of the radiation device for a dedicated machine room.

As shown in FIG. 18, a shielding layer 14 is arranged on the outside of the gantry 1 for surrounding the gantry 1 to shield the radiation rays scattered from the left, right and upper sides of the gantry 1, the shielding chambers 3 (31, 32) are arranged on the front and rear sides of the gantry, the shielding chamber 31 on the front side of the gantry 1 houses the mobile couch body 21 and the support base 22 of the treatment couch 2, the shielding chamber 32 on the rear side of the gantry 1 closes the rear end of the gantry 1, and the front and rear shielding chambers 3 are coupled (directly connected or indirectly connected) with the shielding layer 14 to form a closed body for shielding the radiation rays scattered from the radiation device.

Figure 30:
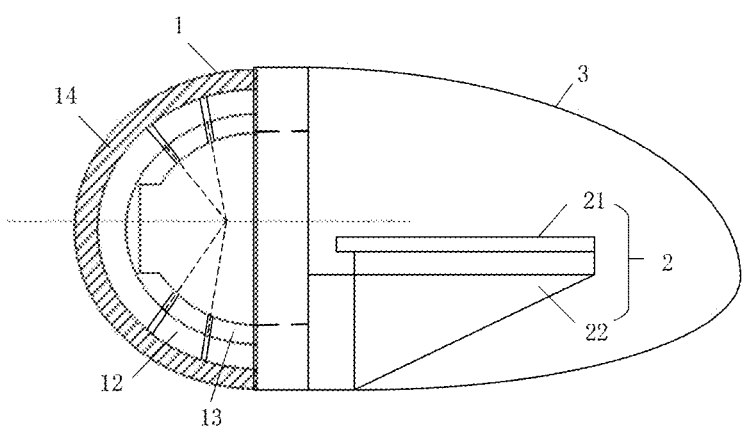
FIG. 30 is a schematic structural diagram of still another radiotherapy device according to an embodiment of the present disclosure.

As shown in FIG. 30, the outside of a source carrier 12 of a radiation source apparatus (i.e., the gantry) is provided with a shielding layer 14 for surrounding the source carrier 12 to shield the radiation rays scattered from the left, right, rear, and upper sides of the radiation source apparatus, the shielding chamber 3 is arranged around the treatment couch 2 to house the mobile couch body 21 and the base 22 of the treatment couch 2, and the shielding chamber 3 is coupled (directly connected or indirectly connected) with the shielding layer 14 to form a closed body for shielding the radiation rays scattered from the radiotherapy device.

According to the embodiment of the present disclosure, the closed shielding chamber is formed by the combination of the shielding chamber and the shielding layer to form self-shielding of the radiation device, thereby eliminating the need for a dedicated machine room. The self-shielding radiation device can be placed at any position, which expands the application scenario of the radiation device.

In the embodiment of the present disclosure, the shielding chamber 3 is detachably coupled with the shielding layer 14, or the shielding chamber 3 is integrally formed with the shielding layer 14. That is: the shielding chamber 3 can be separate from the gantry 1 to serve as an accessory of the radiation device, and installed according to the need of a user; or the shielding chamber 3 can be integrally formed with the gantry 1 to serve as an inherent component of the radiation device.

In the embodiment of the present disclosure, the shielding chamber is adaptively connected with the shielding layer through an adapting structure to achieve coupling.

Figure 7:
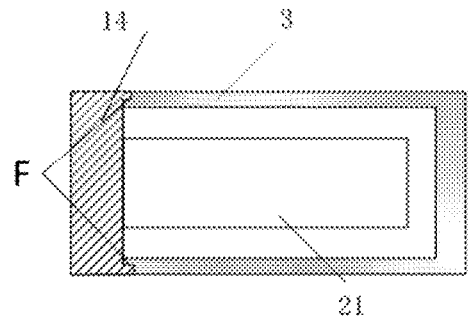
FIG. 7 is a schematic diagram of coupling between a shielding chamber and a shielding layer by an adapting structure according to an embodiment of the present disclosure.

As shown in FIG. 7, the shielding chamber 3 is adaptively connected with the shielding layer 14 through a non-straight splicing interface F, and the adapting structure is the non-straight splicing interface F. As shown in FIG. 7, the non-straight splicing interface F may be a stepped surface, or a curved surface, an S surface, a V-shaped surface, or the like. The embodiment of the present disclosure is not limited to the aforementioned non-straight splicing interface, and may also be implemented by other non-straight splicing interfaces. The non-straight splicing interface described in the embodiment of the present disclosure may realize adaptive connection by using the same interface form or different interface modes. The embodiment of the present disclosure realizes the connection between the shielding chamber and the shielding layer through the non-straight splicing interface, to ensure that no radiation leakage occurs from the interface between the shielding chamber and the shielding layer.

In the embodiment of the present disclosure, the shielding chamber is connected with the shielding layer through an intermediate connector to achieve coupling. The intermediate connector serves as a bridge connecting the shielding chamber with the shielding layer, and the shielding chamber is connected with the shielding layer through the intermediate connector.

Figure 8:
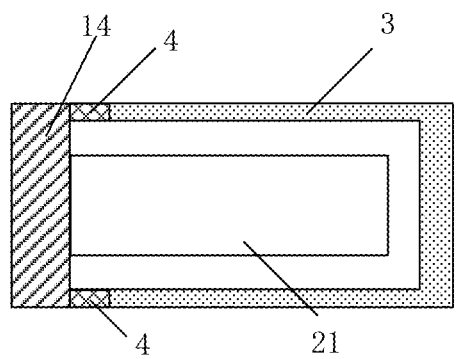
FIG. 8 is a schematic diagram of coupling between the shielding chamber and the shielding layer by an intermediate connector according to an embodiment of the present disclosure.
Figure 9:
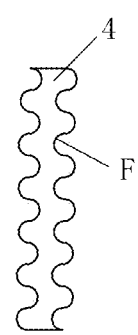
FIG. 9 is a schematic structural diagram of the intermediate connector according to an embodiment of the present disclosure.

As shown in FIG. 8, the intermediate connector 4 is adaptively connected with the shielding chamber 3 through an adapting structure; or, the intermediate connector 4 is adaptively connected with the shielding layer 14 through an adapting structure; or, the intermediate connector 4 is adaptively connected with the shielding chamber 3 and the shielding layer 14 through an adapting structure. According to the embodiment of the present disclosure, the shielding chamber 3 is connected with the shielding layer 14 through the intermediate connector 4 to overcome the mismatch between the shielding chamber 3 and the shielding layer 14 and improve the versatility of the shielding chamber. The adapting structure is a non-straight splicing interface F. As shown in FIG. 9, the non-straight splicing interface F is an S surface, or a curved surface, a stepped surface, a V-shaped surface, or the like. The embodiment of the present disclosure is not limited to the aforementioned non-straight splicing interface, and may also be implemented by other non-straight splicing interface, as long as it can ensure that no radiation leaks at the interface. The non-straight splicing interface described in the embodiment of the present disclosure may realize adaptive connection by using the same interface form or different interface modes.

In an embodiment of the present disclosure, the shielding chamber 3 includes a shielding shell segment, that is, the shielding shell segment is integrally formed, and the shielding chamber is constituted without splicing the shielding shell segment.

Figure 10:
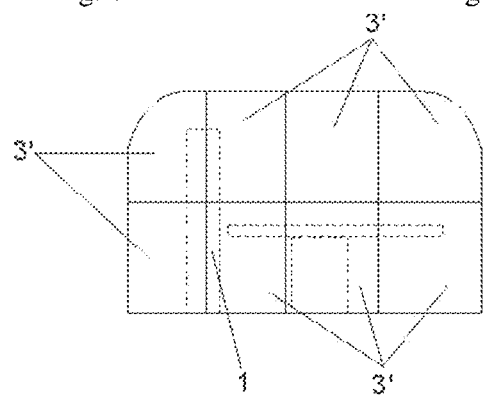
FIG. 10 is a schematic structural diagram of the shielding chamber formed by splicing shielding shell segments according to an embodiment of the present disclosure.

In an embodiment of the present disclosure, as shown in FIG. 10, the shielding chamber 3 includes a plurality of shielding shell segments 3'. According to the embodiment of the present disclosure, the shielding chamber 3 can be constituted by the plurality of shielding shell segments 3', so that the shielding chamber 3 is convenient to transport.

In the embodiment of the present disclosure, the plurality of shielding shell segments 3' are detachably spliced to form the shielding chamber 3. According to the embodiment of the present disclosure, the plurality of shielding shell segments 3' are assembled by means of detachable splicing, so that the installation of the shielding chamber 3 is simpler, and the shielding chamber is flexibly adapted to be used in diverse places.

Figure 11A:
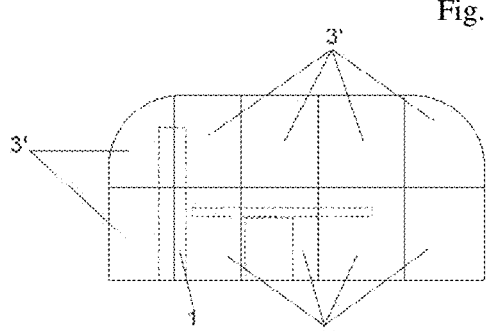
Figure 11B:
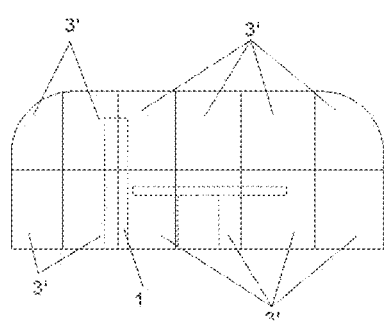

At the same time, as the plurality of shielding shell segments 3' detachably spliced are used to form the shielding chamber 3, the shape and space usage of the shielding chamber can be adjusted according to the installation place and the treatment requirements of the radiation device. Referring to FIGS. 11a-11b, the embodiment of the present disclosure needs to change the shape of the shielding chamber 3, which can be achieved only by increasing or reducing the number of the shielding shell segments 3'. Referring to FIGS. 11c to 11d, the embodiment of the present disclosure needs to expand or reduce the space usage of the shielding chamber 3, which can be achieved by only increasing or reducing the number of the shielding shell segments 3'.

Referring to FIGS. 11e-11f, the embodiment of the present disclosure can also adjust the shape and space usage of the shielding chamber by increasing or reducing shielding shell segments 3' with different sizes or shapes from the original shielding shell segments.

In order to prevent the radiation in the shielding chamber from leaking through the gaps between the plurality of shielding shell segments, as shown in FIG. 12, the interfaces of the plurality of shielding shell segments are non-straight splicing interfaces F.

Specifically, referring to FIG. 12, the non-straight splicing interfaces F of the plurality of shielding shell segments 3' may be curved surfaces, or S surfaces, stepped surfaces, V-shaped surfaces, or the like.

The interfaces described in the embodiment of the present disclosure may be the same interface or different interfaces.

The embodiment of the present disclosure is not limited to the aforementioned interfaces, and may also be implemented by other non-straight splicing interfaces, as long as they can ensure that no radiation leaks at the interfaces.

The shielding chamber described in the embodiment of the present disclosure is made of metal with shielding effect, such as steel, lead, or tungsten.

Figure 13:
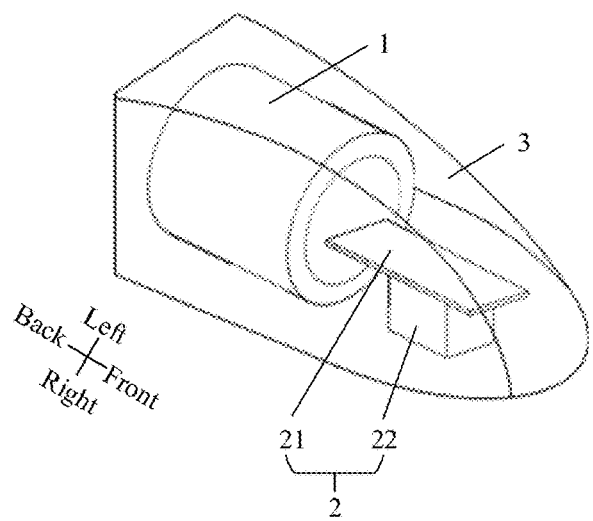
FIG. 13 is a schematic structural diagram of a radiotherapy device according to an embodiment of the present disclosure.

Another embodiment of the present disclosure provides a radiotherapy device, as shown in FIG. 13, including:

A gantry 1, the gantry 1 is used to carry a radiotherapy head, the gantry 1 is of a cylindrical structure, that is, a hollow cylindrical structure with both open ends, such as a drum structure shown in FIG. 13, and the hollow part of the cylindrical structure is used to accommodate a patient;

A treatment couch 2, the treatment couch 2 is used to carry the patient, and the treatment couch 2 can enter the gantry 1 through an opening at one end of the gantry 1;

A shielding chamber 3, the shielding chamber 3 is arranged on the periphery of the radiotherapy device to shield radiation generated by the radiotherapy device.

According to the embodiment of the present disclosure, the shielding chamber is arranged on the periphery of the radiotherapy device, and the shielding chamber at least partially shields scattering radiation generated by the radiotherapy device, which can thus reduce the requirements for radiation shielding of a dedicated machine room or get rid of the dependence of the radiotherapy device on a dedicated machine room.

In an embodiment of the present disclosure, the shielding chamber is arranged on the periphery of the gantry and the treatment couch to form a non-closed body for shielding the radiation generated by the radiotherapy device. The treatment couch includes a mobile couch body and a base.

As shown in FIG. 13, the shielding chamber 3 surrounds the mobile couch body 21 and the base 22 of the treatment couch and the gantry 1 from the front, left and right sides of the radiotherapy device, the rear side of the radiotherapy device is open, and the shielding chamber 3 is used to shield radiation rays scattered from the front, left and right sides of the gantry 1.

Although the shielding chamber in the embodiment of the disclosure does not shield the radiation rays scattered from the rear side of the gantry, it at least reduces the requirements of the radiotherapy device for the machine room. The scattering radiation of the radiotherapy device can be shielded only by radiation shielding transformation on a wall opposite to the rear side of the gantry, which shortens the construction period of the machine room and reduces the construction cost of the machine room.

In addition, since the mobile couch body 21 and the base 22 of the treatment couch 2 are both housed within the shielding chamber 3, the space available for the patient in the entire shielding chamber is increased, which helps to alleviate the patient's symptom of claustrophobia.

The embodiment of the present disclosure does not limit the form of the non-closed shielding chamber, and the non-closed shielding chamber may also be open on the front, rear or left side, which is not limited in the embodiment of the present disclosure.

In another embodiment of the present disclosure, the shielding chamber is arranged on the periphery of the gantry and the treatment couch to form a closed body for shielding the radiation generated by the radiotherapy device. The treatment couch includes a mobile couch body and a base.

Figure 14:
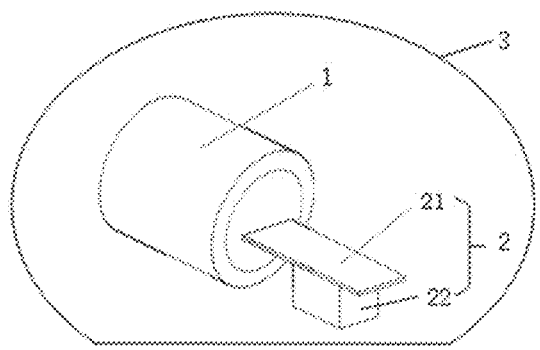
FIG. 14 is a schematic diagram of another radiotherapy device according to an embodiment of the present disclosure.

As shown in FIG. 14, the shielding chamber 3 completely houses the gantry 1, the mobile couch body 21 and the base 22, that is, the shielding chamber 3 surrounds the radiotherapy device to form a closed body. The shielding chamber 3 can shield the radiation rays scattered from the front, left, rear, and right sides of the gantry 1.

According to the embodiment of the present disclosure, the closed shielding chamber is arranged around the radiotherapy device to form self-shielding of the radiotherapy device, thereby eliminating the need for a dedicated machine room. The self-shielding radiotherapy device can be placed at any position, which expands the application scenario of the radiotherapy device.

In addition, since the mobile couch body 21 and the base 22 of the treatment couch 2 are both housed within the shielding chamber 3, the space available for the patient in the entire shielding chamber 3 is increased, which helps to alleviate the patient's symptom of claustrophobia.

Figure 15:
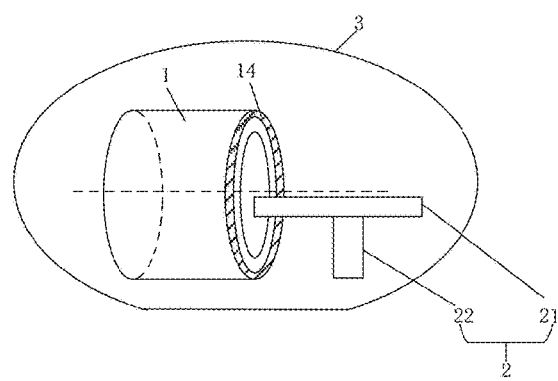
FIG. 15 is a schematic diagram of still another radiotherapy device according to an embodiment of the present disclosure.
Figure 16:
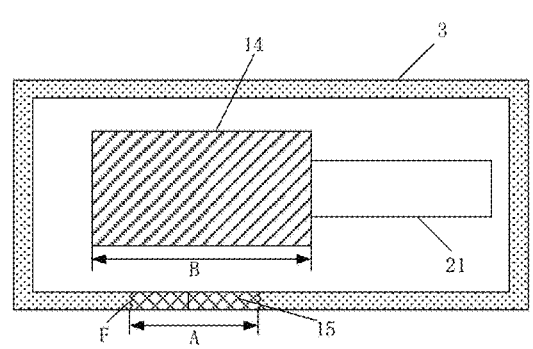
FIG. 16 is a top view of FIG. 15.

According to an embodiment of the present disclosure, as shown in FIGS. 15 and 16, the peripheral surface of the gantry 1 is provided with a shielding layer 14, the shielding chamber 3 has at least one entrance 15, the entrance 15 is a third openable shielding door, the third openable shielding door is arranged at a position of the shielding chamber 3 opposite to the shielding layer 14, and the opening size A of the third openable shielding door is smaller than the size B of the shielding layer 14 in the axial direction of the gantry.

As shown in FIGS. 15 and 16, the peripheral surface of the gantry 1 is provided with a shielding layer 14, the shielding layer 14 has the same width as the gantry 1 in the axis direction of the gantry and is used to shield radiation rays scattered from the left, right and upper sides of the gantry 1, the shielding chamber 3 completely houses the gantry 1, the mobile couch body 21 and the base 22, the shielding chamber 3 has an entrance 15, the entrance 15 is a third openable shielding door, the third openable shielding door is arranged on a side wall of the shielding chamber 3 and faces the shielding layer 14, and the opening size A of the third openable shielding door (i.e., the size of the third openable shielding door in the axial direction of the gantry) is smaller than the size B of the shielding layer 14 in the axis direction of the gantry, so that when the third openable shielding door is opened, the radiation rays at the opening are shielded by the shielding layer 14, and the radiation rays in the shielding chamber 3 will not leak from the opening of the third openable shielding door.

The interface F between the third openable shielding door and the shielding chamber 3 is a non-straight splicing interface, to ensure that radiation rays will not leak from the interface between the shielding door and the shielding chamber 3. As shown in FIG. 16, the non-straight splicing interface F may be a V-shaped surface, or a curved surface, an S surface, or a stepped surface. The embodiment of the present disclosure is not limited to the aforementioned non-straight splicing interface, and may also be implemented by other non-straight splicing interfaces.

In yet another embodiment of the present disclosure, the peripheral surface of the gantry is provided with a shielding layer, the shielding chamber is arranged on the periphery of the treatment couch, and the shielding layer is coupled with the shielding chamber to shield the radiation generated by the radiotherapy device.

Figure 17:
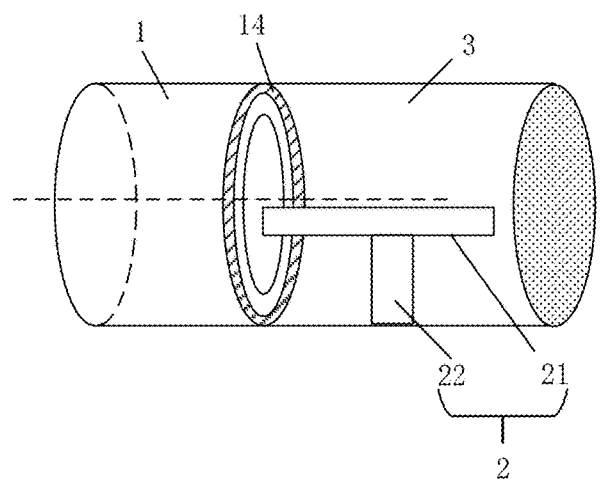
FIG. 17 is a schematic diagram of still another radiotherapy device according to an embodiment of the present disclosure.

As shown in FIG. 17, the peripheral surface of the gantry 1 is provided with a shielding layer 14 for shielding the radiation rays scattered from the left, right and upper sides of the gantry 1, the shielding chamber 3 surrounds the treatment couch 2 to house the mobile couch body 21 and the base 22 of the treatment couch, and the shielding chamber 3 is coupled (directly connected or indirectly connected) with the shielding layer 14 to shield the radiation rays scattered from the front, left, right and upper sides of the gantry 1.

The embodiment of the present disclosure shields some of the radiation rays scattered around the radiotherapy device through the combination of the shielding chamber and the shielding layer, which reduces the requirements of the radiotherapy device for the machine room, shortens the construction period of the machine room, and reduces the construction cost of the machine room.

In the embodiment of the present disclosure, the gantry includes a shielding layer, the shielding chamber includes a first shielding chamber and a second shielding chamber, the first shielding chamber and the second shielding chamber are on both sides of the gantry in the axis direction, and the first shielding chamber and the second shielding chamber are respectively coupled with the shielding layer to form a closed body for shielding the radiation generated by the radiotherapy device.

As shown in FIG. 18, the peripheral surface of the gantry 1 is provided with a shielding layer 14 for shielding the radiation rays scattered from the left, right and upper sides of the gantry 1, the shielding chamber 3 includes a first shielding chamber 31 and a second shielding chamber 32 on both sides in the axis direction, the first shielding chamber 31 and the second shielding chamber 32 are respectively coupled (directly connected or indirectly connected) with the shielding layer 14 to form a closed body, wherein the mobile couch body 21 and the base 22 of the treatment couch are also housed within the closed body, and the shielding chamber 3 is combined with the shielding layer 14 to form the closed body for shielding the radiation rays scattered from the front, left, rear, right and upper sides of the gantry 1.

According to the embodiment of the present disclosure, the closed shielding chamber is formed by the combination of the first shielding chamber 31, the second shielding chamber 32 and the shielding layer 14 to form self-shielding of the radiotherapy device, thereby eliminating the need for a dedicated machine room. The self-shielding radiotherapy device can be placed at any position, which expands the application scenario of the radiotherapy device.

In the embodiment of the present disclosure, the shielding chamber 3 (or 31, 32) is detachably coupled with the shielding layer 14, or the shielding chamber 3 (or 31, 32) is integrally formed with the shielding layer 14. That is: the shielding chamber 3 (or 31, 32) can be separated from the gantry 1 to serve as an accessory of the radiotherapy device, and installed according to the need of a user; or, the shielding chamber 3 (or 31, 32) can be integrally formed with the gantry 1 to serve as an inherent component of the radiotherapy device.

In the embodiment of the present disclosure, the shielding chamber 3 (or 31, 32) is adaptively connected with the shielding layer 14 through an adapting structure to achieve coupling.

As shown in FIG. 19, the shielding chambers 31, 32 are adaptively connected with the shielding layer 14 through non-straight splicing interfaces F, and the adapting structure is the non-straight splicing interface F. As shown in FIG. 19, the non-straight splicing interface F may be a stepped surface, or a curved surface, an S surface, a V-shaped surface, or the like. The embodiment of the present disclosure is not limited to the aforementioned non-straight splicing interface, and may also be implemented by other non-straight splicing interfaces. The non-straight splicing interface described in the embodiment of the present disclosure may realize adaptive connection by using the same interface form or different interface modes. The embodiment of the present disclosure realizes the connection between the shielding chamber and the shielding layer through the non-straight splicing interface, to ensure that no radiation leakage occurs from the interface between the shielding chamber and the shielding layer.

In the embodiment of the present disclosure, as shown in FIG. 20, the shielding chamber 3 (or 31, 32) is connected with the shielding layer 14 through an intermediate connector 4 to achieve coupling. The intermediate connector 4 serves as a bridge connecting the shielding chamber 3 (or 31, 32) with the shielding layer 14, and the shielding chamber 3 (or 31, 32) is connected with the shielding layer 14 through the intermediate connector 4.

As shown in FIG. 21, the intermediate connector 4 is adaptively connected with the shielding chamber 3 (or 31, 32) through an adapting structure; or, the intermediate connector 4 is adaptively connected with the shielding layer 14 through an adapting structure; or, the intermediate connector 4 is adaptively connected with the shielding chamber 3 (or 31, 32) and the shielding layer 14 through an adapting structure. According to the embodiment of the present disclosure, the shielding chamber 3 (or 31, 32) is connected with the shielding layer 14 through the intermediate connector 4 to overcome the mismatch between the shielding chamber and the shielding layer and improve the versatility of the shielding chamber. The adapting structure is a non-straight splicing interface F. As shown in FIG. 21, the non-straight splicing interface F is an S surface, or a curved surface, a stepped surface, a V-shaped surface, or the like. The embodiment of the present disclosure is not limited to the aforementioned non-straight splicing interface, and may also be implemented by other non-straight splicing interface, as long as it can ensure that no radiation leaks at the interface. The non-straight splicing interface described in the embodiment of the present disclosure may realize adaptive connection by using the same interface form or different interface modes.

In an embodiment of the present disclosure, as shown in FIG. 22, the shielding chamber 3 includes a plurality of shielding shell segments 3'. According to the embodiment of the present disclosure, the shielding chamber 3 can be constituted by the plurality of shielding shell segments 3', so that the shielding chamber 3 is more convenient to transport.

In the embodiment of the present disclosure, the plurality of shielding shell segments 3' are detachably spliced to form the shielding chamber 3. According to the embodiment of the present disclosure, the plurality of shielding shell segments are assembled by means of detachable splicing, so that the installation of the shielding chamber is simpler, and the shielding chamber is flexibly adapted to be used in diverse places.

Figure 23A:
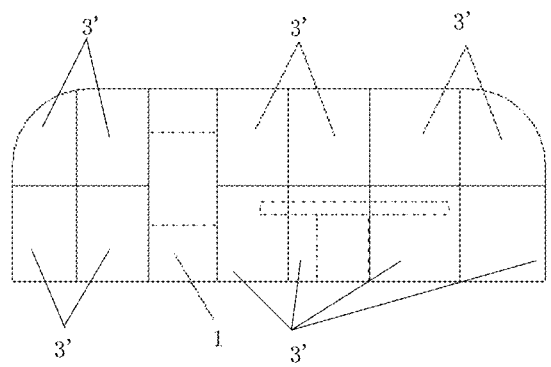
FIGS. 23a-23f are schematic diagrams of the shielding chamber formed by splicing different shielding shell segments according to an embodiment of the present disclosure.
Figure 23B:
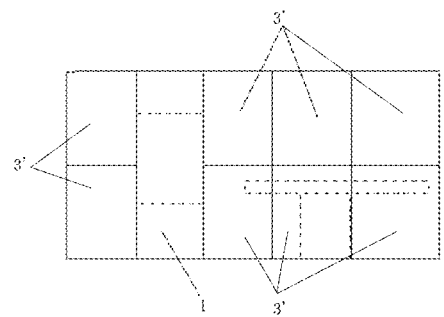
Figure 23C:
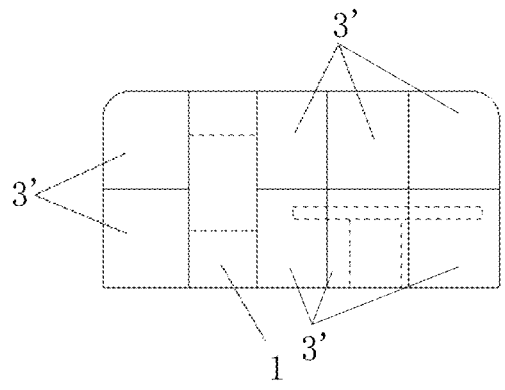
Figure 23D:
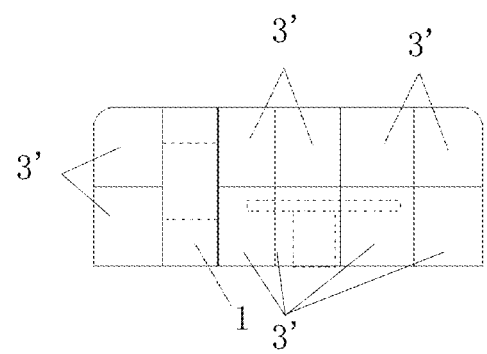

At the same time, as the plurality of shielding shell segments detachably spliced are used to form the shielding chamber, the shape and space usage of the shielding chamber can be adjusted according to the installation place and the treatment requirements of the radiotherapy device. Referring to FIGS. 23a to 23b, the embodiment of the present disclosure needs to change the shape of the shielding chamber, which can be achieved only by increasing or reducing the number of the shielding shell segments 3'. Referring to FIGS. 23c to 23d, the embodiment of the present disclosure needs to expand or reduce the space usage of the shielding chamber, which can be achieved by only increasing or reducing the number of the shielding shell segments 3'.

Figure 23E:
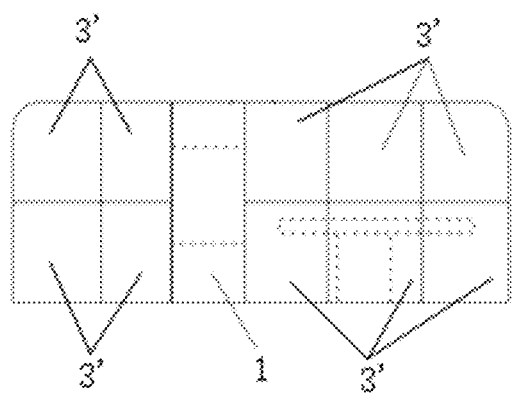
Figure 23F:
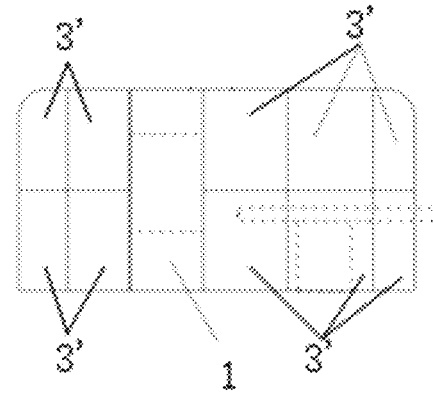

Referring to FIGS. 23e-23f, the embodiment of the present disclosure can also adjust the shape and space usage of the shielding chamber by increasing or reducing shielding shell segments 3' with different sizes or shapes from the original shielding shell segments 3'.

Figure 24:
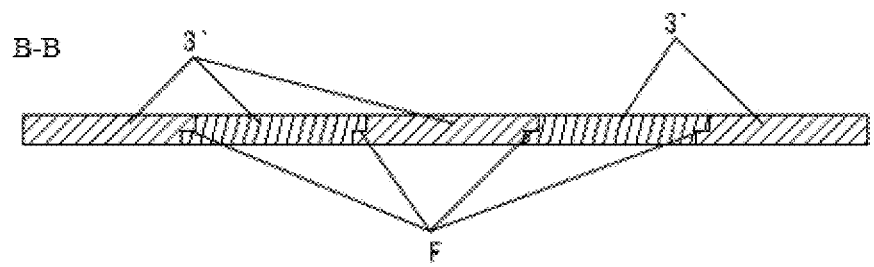
FIG. 24 is a schematic cross sectional view of splicing a plurality of spliced shielding shell segments taken along the line B-B of FIG. 22 according to an embodiment of the present disclosure.

In order to prevent the radiation in the shielding chamber from leaking through the gaps between the plurality of shielding shell segments, as shown in FIG. 24, the interfaces of the plurality of shielding shell segments are non-straight splicing interfaces F.

Specifically, referring to FIG. 24, the interfaces of the plurality of shielding shell segments 3' may be curved surfaces, or S surfaces, stepped surfaces, V-shaped surfaces, or the like.

The interfaces described in the embodiment of the present disclosure may be the same interface or different interfaces.

The embodiment of the present disclosure is not limited to the aforementioned interfaces, and may also be implemented by other non-straight splicing interfaces, as long as they can ensure that no radiation leaks at the interfaces.

The shielding chamber described in the embodiment of the present disclosure is made of metal with shielding effect, such as steel, lead, or tungsten.

Figure 25:
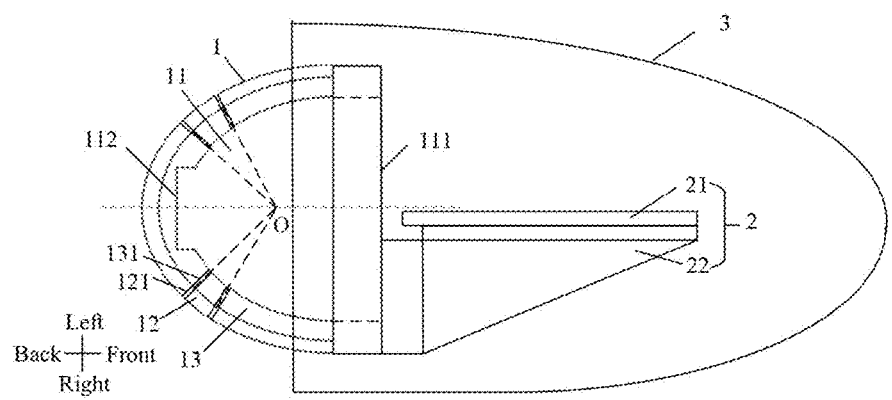
FIG. 25 is a schematic structural diagram of a radiotherapy device according to an embodiment of the present disclosure.
Figure 26:
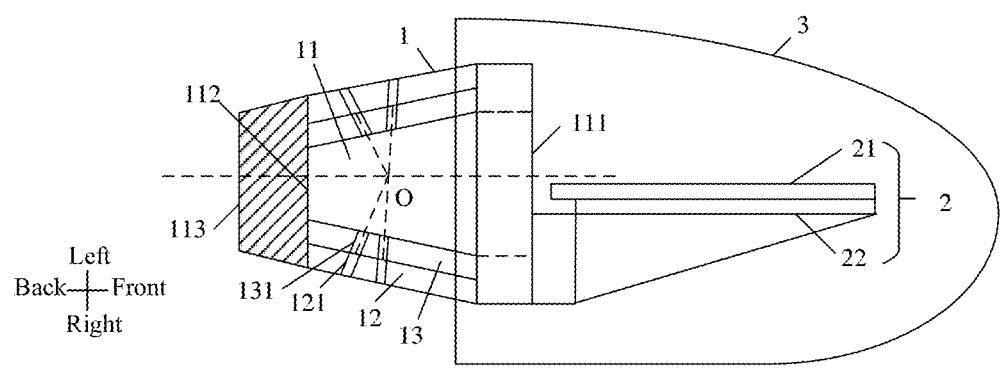
FIG. 26 is a schematic structural diagram of another radiotherapy device according to an embodiment of the present disclosure.

Another embodiment of the present disclosure provides a radiotherapy device. As shown in FIGS. 25 and 26, the radiotherapy device includes:

A radiation source apparatus 1 (i.e., a gantry), a treatment cavity 11 is formed in the radiation source apparatus 1, one end of the radiation source apparatus 1 has an opening 111 for the treatment couch 2 to enter and exit the treatment cavity, and the end of the treatment cavity 11 opposite to the opening 111 is a closed end 112;

A treatment couch 2, used to carry a patient and move the patient into or out of the treatment cavity 11;

A shielding chamber 3, arranged on the periphery of the radiotherapy device to shield radiation generated by the radiotherapy device.

According to the embodiment of the present disclosure, the shielding chamber is arranged on the periphery of the radiotherapy device, and the shielding chamber at least partially shields scattering radiation generated in the radiotherapy device, which can thus reduce the requirements for radiation shielding of a dedicated machine room or get rid of the dependence of the radiotherapy device on a dedicated machine room.

In an embodiment of the present disclosure, as shown in FIG. 25, the radiation source apparatus 1 includes a source carrier 12 and a collimator 13, both the source carrier 12 and the collimator 13 have a hemispherical structure, the collimator 13 is arranged on the inner side of the source carrier 12, the inner cavity of the collimator 13 forms the treatment cavity 11 of the radiation source apparatus, the treatment cavity 11 is used to accommodate the patient, the source carrier 12 is provided with a radiation source 121, the collimator 13 is provided with a collimating hole 131 corresponding to the radiation source, and the radiation emitted by the radiation source 121 passes through the collimating hole 131 to focus on a focal point O in the treatment cavity 11. The open ends of the hemispherical carrier 12 and the collimator 13 allow the treatment couch 2 to enter and exit the treatment cavity 11, thus forming an opening 111 of the treatment cavity 11. The closed ends of the hemispherical source carrier 12 and collimator 13 constitute a closed end 112 of the treatment cavity 11.

In an embodiment of the present disclosure, as shown in FIG. 26, the radiation source apparatus 1 includes a source carrier 12 and a collimator 13, both the source carrier 12 and the collimator 13 have a hollow cylindrical structure (e.g., cone), the collimator 13 is arranged on the inner side of the source carrier 12, the inner cavity of the collimator 13 forms the treatment cavity 11 of the radiation source apparatus 1, the treatment cavity 11 is used to accommodate a patient, the source carrier 12 is provided with a radiation source 121, the collimator 13 is provided with a collimating hole 131 corresponding to the radiation source 121, and the radiation emitted by the radiation source 121 passes through the collimating hole 131 to focus on a focal point O in the treatment cavity 11. One ends of the hollow cylindrical source carrier 12 and collimator 13 allow the treatment couch 2 to enter and exit the treatment cavity 11, thus forming an opening 111 of the treatment cavity 11. The other ends of the hollow cylindrical source carrier 12 and collimator 13 are blocked by a shielding plug 113, thus forming a closed end 112 of the treatment cavity 11.

In an embodiment of the present disclosure, the shielding chamber is arranged on the periphery of the radiation source apparatus and the treatment couch to form a non-closed body for shielding the radiation generated by the radiotherapy device.

The treatment couch 2 includes a mobile couch body and a base.

As shown in FIGS. 25 and 26, the shielding chamber 3 surrounds the mobile couch body 21 and the base 22 of the treatment couch 2 and the radiation source apparatus from the front, left and right sides of the radiotherapy device, the rear side of the radiotherapy device is open, and the shielding chamber 3 is used to shield radiation rays scattered from the front, left and right sides of the radiation source apparatus.

Although the shielding chamber in the embodiment of the disclosure does not shield the radiation rays scattered from the rear side of the radiation source apparatus, it at least reduces the requirements of the radiotherapy device for the machine room. The scattering radiation of the radiotherapy device can be shielded only by radiation shielding transformation on a wall opposite to the rear side of the radiation source apparatus, which shortens the construction period of the machine room and reduces the construction cost of the machine room.

In addition, since the mobile couch body 21 and the base 22 of the treatment couch 2 are both housed within the shielding chamber 3, the space available for the patient in the entire shielding chamber 3 is increased, which helps to alleviate the patient's symptom of claustrophobia.

The embodiment of the present disclosure does not limit the form of the non-closed shielding chamber, and the non-closed shielding chamber may also be open on the front, rear or left side, which is not limited in the embodiment of the present disclosure.

In an embodiment of the present disclosure, the shielding chamber is arranged on the periphery of the radiation source apparatus and the treatment couch to form a closed body for shielding the radiation generated by the radiotherapy device.

The treatment couch 2 includes a mobile couch body and a base.

Figure 27:
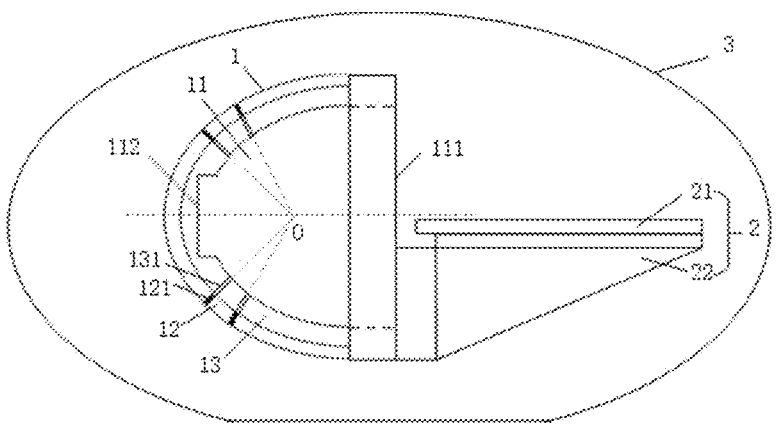
FIG. 27 is a schematic structural diagram of still another radiotherapy device according to an embodiment of the present disclosure.

As shown in FIG. 27, the shielding chamber 3 completely houses the radiation source apparatus 1, the mobile couch body 21 and the base 22, that is, the shielding chamber 3 surrounds the radiotherapy device to form a closed body. The shielding chamber 3 can shield the radiation rays scattered from the front, left, rear, and right sides of the radiation source apparatus.

According to the embodiment of the present disclosure, the closed shielding chamber is arranged around the radiotherapy device to form self-shielding of the radiotherapy device, thereby eliminating the need for a dedicated machine room. The self-shielding radiotherapy device can be placed at any position, which expands the application scenario of the radiotherapy device.

In addition, since the mobile couch body 21 and the base 22 of the treatment couch 2 are both housed within the shielding chamber 3, the space available for the patient in the entire shielding chamber 3 is increased, which helps to alleviate the patient's symptom of claustrophobia.

The radiation source apparatus in the embodiment of the present disclosure includes a shielding layer, the shielding chamber has at least one entrance, the entrance is a third openable shielding door, the third openable shielding door is arranged at a position of the shielding chamber opposite to the shielding layer of the radiation source apparatus, and the opening size of the third openable shielding door is smaller than the size of the shielding layer of the radiation source apparatus in the axial direction of the radiation source apparatus.

Figure 28:
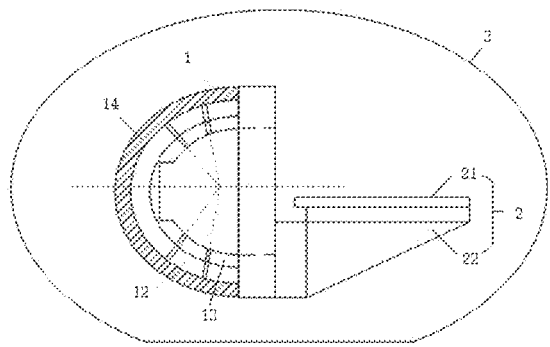
FIG. 28 is a schematic structural diagram of still another radiotherapy device according to an embodiment of the present disclosure.
Figure 29:
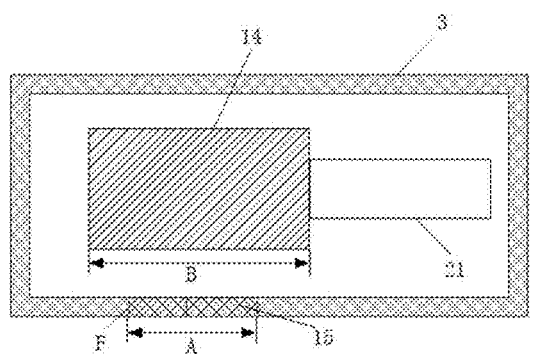
FIG. 29 is a top view of FIG. 28.

As shown in FIGS. 28 and 29, the outside of the source carrier 12 of the radiation source apparatus is provided with a shielding layer 14 for surrounding the source carrier 12 to shield radiation rays scattered from the left, right, rear, and upper sides of the radiation source apparatus 1, the shielding chamber 3 completely houses the radiation source apparatus 1, the mobile couch body 21 and the base 22, the shielding chamber 3 has an entrance 15, the entrance 15 is a third openable shielding door, the third openable shielding door is arranged on a side wall of the shielding chamber 3 and faces the shielding layer 14 of the radiation source apparatus, and the opening size A of the third openable shielding door (i.e., the size of the third openable shielding door in the axial direction of the radiation source apparatus) is smaller than the size B of the shielding layer 14 of the radiation source apparatus in the axial direction of the radiation source apparatus, so that when the third openable shielding door is opened, the radiation rays at the opening are shielded by the shielding layer 14 of the radiation source apparatus, and the radiation rays in the shielding chamber 3 will not leak from the opening of the third openable shielding door.

The interface F between the third openable shielding door and the shielding chamber 3 is a non-straight splicing interface, to ensure that radiation rays will not leak from the interface between the shielding door and the shielding chamber. As shown in FIG. 29, the non-straight splicing interface F may be a V-shaped surface, or a curved surface, an S surface, or a stepped surface. The embodiment of the present disclosure is not limited to the aforementioned non-straight splicing interface, and may also be implemented by other non-straight splicing interfaces.

In an embodiment of the present disclosure, the radiation source apparatus includes a shielding layer, the shielding chamber is arranged on the periphery of the treatment couch, and the shielding layer is coupled with the shielding chamber to form a closed body for shielding the radiation generated by the radiotherapy device.

As shown in FIG. 30, the outside of the source carrier 12 of the radiation source apparatus is provided with a shielding layer 14 for surrounding the source carrier 12 to shield the radiation rays scattered from the left, right, rear, and upper sides of the radiation source apparatus, the shielding chamber 3 is arranged around the treatment couch 2 to house the mobile couch body 21 and the base 22 of the treatment couch 2, and the shielding chamber 3 is coupled (directly connected or indirectly connected) with the shielding layer 14 to form a closed body for shielding the radiation rays scattered from the radiotherapy device.

According to the embodiment of the present disclosure, the closed shielding chamber is formed by the combination of the shielding chamber and the shielding layer to form self-shielding of the radiotherapy device, thereby eliminating the need for a dedicated machine room. The self-shielding radiotherapy device can be placed at any position, which expands the application scenario of the radiotherapy device.

In the embodiment of the present disclosure, the shielding chamber 3 is detachably coupled with the shielding layer 14, or the shielding chamber 3 is integrally formed with the shielding layer 14. That is, the shielding chamber 3 can be separated from the radiation source apparatus 1 to serve as an accessory of the radiotherapy device, and installed according to the need of a user; or, the shielding chamber 3 can be integrally formed with the radiation source apparatus 1 to serve as an inherent component of the radiotherapy device.

In the embodiment of the present disclosure, the shielding chamber is adaptively connected with the shielding layer through an adapting structure to achieve coupling.

As shown in FIG. 31, the shielding chamber 3 is adaptively connected with the shielding layer 14 through a non-straight splicing interface F, and the adapting structure is the non-straight splicing interface F. As shown in FIG. 31, the non-straight splicing interface F may be a stepped surface, or a curved surface, an S surface, a V-shaped surface, or the like. The embodiment of the present disclosure is not limited to the aforementioned non-straight splicing interface, and may also be implemented by other non-straight splicing interfaces. The non-straight splicing interface described in the embodiment of the present disclosure may realize adaptive connection by using the same interface form or different interface modes. The embodiment of the present disclosure realizes the connection between the shielding chamber and the shielding layer through the non-straight splicing interface, to ensure that no radiation leakage occurs from the interface between the shielding chamber and the shielding layer.

In the embodiment of the present disclosure, the shielding chamber is connected with the shielding layer through an intermediate connector to achieve coupling. The intermediate connector serves as a bridge connecting the shielding chamber with the shielding layer, and the shielding chamber is connected with the shielding layer through the intermediate connector.

As shown in FIG. 32, the intermediate connector 4 is adaptively connected with the shielding chamber 3 through an adapting structure; or, the intermediate connector 4 is adaptively connected with the shielding layer 14 through an adapting structure; or, the intermediate connector 4 is adaptively connected with the shielding chamber 3 and the shielding layer 14 through an adapting structure. According to the embodiment of the present disclosure, the shielding chamber 3 is connected with the shielding layer 14 through the intermediate connector 4 to overcome the mismatch between the shielding chamber 3 and the shielding layer 14 and improve the versatility of the shielding chamber. The adapting structure is a non-straight splicing interface F. As shown in FIG. 33, the non-straight splicing interface F is an S surface, or a curved surface, a stepped surface, a V-shaped surface, or the like. The embodiment of the present disclosure is not limited to the aforementioned non-straight splicing interface, and may also be implemented by other non-straight splicing interface, as long as it can ensure that no radiation leaks at the interface. The non-straight splicing interface described in the embodiment of the present disclosure may realize adaptive connection by using the same interface form or different interface modes.

In an embodiment of the present disclosure, as shown in FIG. 34, the shielding chamber 3 includes a plurality of shielding shell segments 3'. According to the embodiment of the present disclosure, the shielding chamber 3 can be constituted by the plurality of shielding shell segments 3', so that the shielding chamber 3 is more convenient to transport.

In the embodiment of the present disclosure, the plurality of shielding shell segments 3' are detachably spliced to form the shielding chamber 3. According to the embodiment of the present disclosure, the plurality of shielding shell segments 3' are assembled by means of detachable splicing, so that the installation of the shielding chamber 3 is simpler, and the shielding chamber is flexibly adapted to be used in diverse places.

At the same time, as the plurality of shielding shell segments 3' detachably spliced are used to form the shielding chamber 3, the shape and space usage of the shielding chamber can be adjusted according to the installation place and the treatment requirements of the radiotherapy device. Referring to FIGS. 35a-35b, the embodiment of the present disclosure needs to change the shape of the shielding chamber 3, which can be achieved only by increasing or reducing the number of the shielding shell segments 3'. Referring to FIGS. 35c to 35d, the embodiment of the present disclosure needs to expand or reduce the space usage of the shielding chamber 3, which can be achieved by only increasing or reducing the number of the shielding shell segments 3'.

Referring to FIGS. 35e-35f, the embodiment of the present disclosure can also adjust the shape and space usage of the shielding chamber by increasing or reducing shielding shell segments 3' with different sizes or shapes from the original shielding shell segments 3'.

In order to prevent the radiation in the shielding chamber from leaking through the gaps between the plurality of shielding shell segments, as shown in FIG. 36, the interfaces of the plurality of shielding shell segments are non-straight splicing interfaces F.

Specifically, referring to FIG. 36, the interfaces F of the plurality of shielding shell segments 3' may be curved surfaces, or S surfaces, stepped surfaces, V-shaped surfaces, or the like.

The interfaces described in the embodiment of the present disclosure may be the same interface or different interfaces.

The embodiment of the present disclosure is not limited to the aforementioned interfaces, and may also be implemented by other non-straight splicing interfaces, as long as they can ensure that no radiation leaks at the interfaces.

The shielding chamber described in the embodiment of the present disclosure is made of metal with shielding effect, such as steel, lead, or tungsten.

An embodiment of the present disclosure provides a radiotherapy device, as shown in FIG. 37, including:

A treatment couch 2, the treatment couch 2 includes a mobile couch body 21 and a support base 22, and the support base 22 is used to support the movement of the mobile couch body 21;

A shielding chamber 3, the shielding chamber 3 is arranged on the periphery of the mobile couch body 21 and the support base 22 to shield radiation generated by the radiotherapy device.

According to the embodiment of the present disclosure, the shielding chamber is arranged on the periphery of the treatment couch to at least partially shield scattering radiation generated by the radiotherapy device on the treatment couch side, which can thus reduce the requirements for radiation shielding of a dedicated machine room or get rid of the dependence of the radiotherapy device on a dedicated machine room.

In addition, since the mobile couch body and the support base of the treatment couch are both housed within the shielding chamber, the space available for the patient in the entire shielding chamber is increased, which helps to alleviate the patient's symptom of claustrophobia.

In an embodiment of the present disclosure, the radiotherapy device further includes a gantry 1, the gantry 1 is configured to carry a radiation source, and the shielding chamber 3 is arranged on the periphery of the mobile couch body 21, the support base 22 and the gantry 1 to form a closed body for shielding the radiation generated by the radiotherapy device.

As shown in FIG. 38, the shielding chamber 3 is arranged on the periphery of the radiotherapy device to completely house the gantry 1, the mobile couch body 21 and the support base 22, thus forming a closed body. The shielding chamber 3 can shield the radiation rays scattered from the front, left, rear, and right sides of the gantry 1.

According to the embodiment of the present disclosure, the closed shielding chamber is arranged around the radiotherapy device to form self-shielding of the radiotherapy device, thereby eliminating the need for a dedicated machine room. The self-shielding radiotherapy device can be placed at any position, which expands the application scenario of the radiotherapy device.

In addition, since the mobile couch body and the support base of the treatment couch are both housed within the shielding chamber, the space available for the patient in the entire shielding chamber is increased, which helps to alleviate the patient's symptom of claustrophobia.

According to the embodiment of the present disclosure, a shielding layer is arranged on the outside of the gantry, the shielding chamber has at least one entrance, the entrance is a third openable shielding door, the third openable shielding door is arranged at a position of the shielding chamber opposite to the shielding layer of the gantry, and the opening size of the third openable shielding door is smaller than the size of the shielding layer of the gantry in the axial direction of the gantry.

Figure 39:
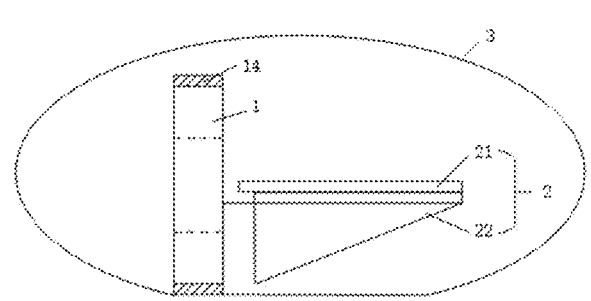
FIG. 39 is a schematic diagram of still another radiotherapy device according to an embodiment of the present disclosure.
Figure 40:
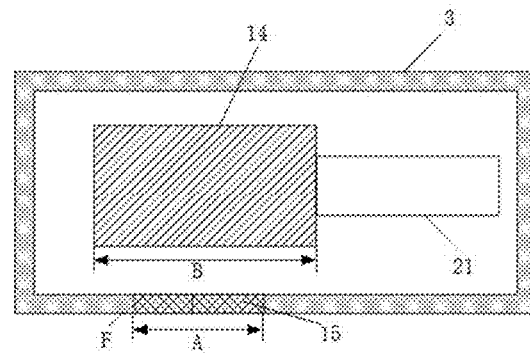
FIG. 40 is a top view of FIG. 39.

As shown in FIGS. 39 and 40, a shielding layer 14 is arranged on the outside of the gantry 1, the shielding layer 14 has the same width as the gantry 1 in the axis direction of the gantry and is used to shield radiation rays scattered from the left, right and upper sides of the gantry 1, the shielding chamber 3 completely houses the gantry 1, the mobile couch body 21 and the support base 22, the shielding chamber 3 has an entrance 15, the entrance 15 is a third openable shielding door, the third openable shielding door is arranged on a side wall of the shielding chamber 3 and faces the shielding layer 14 of the gantry, and the opening size A of the third openable shielding door (i.e., the size of the third openable shielding door in the axial direction of the gantry) is smaller than the size B of the shielding layer 14 of the gantry in the axial direction of the gantry, so that when the third openable shielding door is opened, the radiation rays at the opening are shielded by the shielding layer 14 of the gantry, and the radiation rays in the shielding chamber 3 will not leak from the opening of the third openable shielding door.

The interface between the third openable shielding door and the shielding chamber 3 is a non-straight splicing interface to ensure that radiation rays will not leak from the interface between the shielding door and the shielding chamber.

In an embodiment of the present disclosure, the radiotherapy device further includes a gantry configured to carry a radiation source, the gantry includes a shielding layer, and the shielding chamber is coupled with the shielding layer to form a closed body for shielding the radiation generated by the radiotherapy device.

Figure 41:
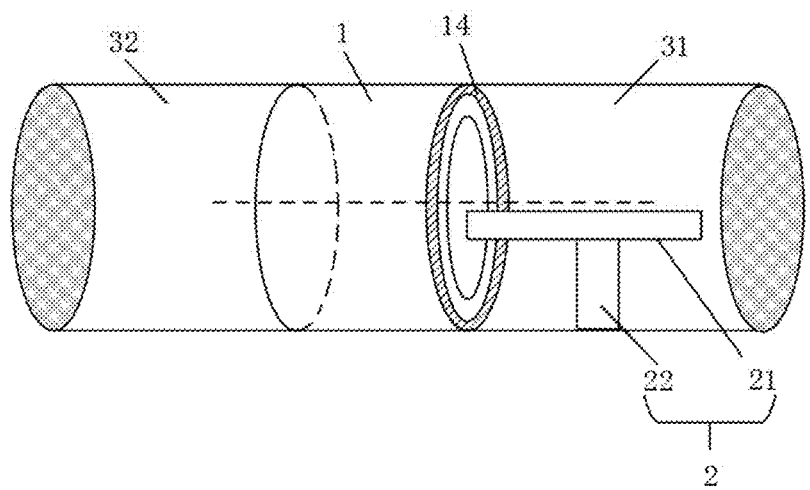
FIG. 41 is a schematic diagram of still another radiotherapy device according to an embodiment of the present disclosure.

In the embodiment of the present disclosure, the gantry is of a hollow cylindrical structure with both open ends. As shown in FIG. 41, the gantry 1 is a drum-type gantry, the outside of the drum-type gantry is provided with a shielding layer 14, the shielding chamber 3 includes a first shielding chamber 31 and a second shielding chamber 32, the first shielding chamber 31 and the second shielding chamber 32 are on both sides of the gantry 1 in the axis direction, and the first shielding chamber 31 and the second shielding chamber 32 are respectively coupled (directly connected or indirectly connected) with the shielding layer 14 to form a closed body for shielding the radiation generated by the radiotherapy device. The first shielding chamber 31 is used to house the treatment couch 2, and the second shielding chamber 32 is used to block the scattering radiation on the rear side of the gantry 1.

The embodiment of the present disclosure does not limit the shapes of the first shielding chamber and the second shielding chamber.

According to the embodiment of the present disclosure, the closed shielding chamber is formed by the combination of the first shielding chamber 31, the second shielding chamber 32 and the shielding layer 14 to form self-shielding of the radiotherapy device, thereby eliminating the need for a dedicated machine room. The self-shielding radiotherapy device can be placed at any position, which expands the application scenario of the radiotherapy device.

In the embodiment of the present disclosure, a treatment cavity is formed in the gantry, one end of the gantry has an opening for the treatment couch to enter and exit the treatment cavity, and the end of the treatment cavity opposite to the opening is closed.

Figure 42:
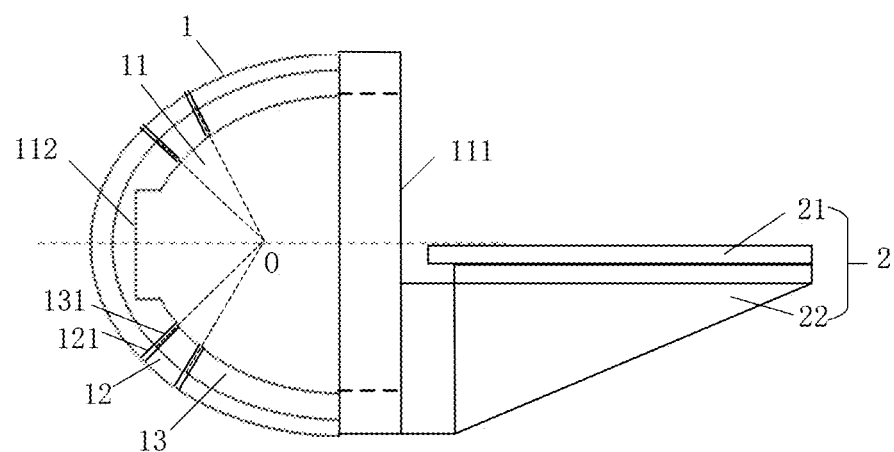
FIG. 42 is a schematic structural diagram of a gantry of a radiotherapy device according to an embodiment of the present disclosure.

As shown in FIG. 42, the gantry 1 according to the embodiment of the present disclosure includes a source carrier 12 and a collimator 13, both the source carrier 12 and the collimator 13 have a hemispherical structure, the collimator 13 is arranged on the inner side of the source carrier 12, the inner cavity of the collimator 13 forms the treatment cavity 11 in the gantry 1, the treatment cavity 11 is used to accommodate a patient, the source carrier 12 is provided with a radiation source 121, the collimator 13 is provided with a collimating hole 131 corresponding to the radiation source 121, and the radiation emitted by the radiation source 121 passes through the collimating hole 131 to focus on a focal point O in the treatment cavity 11. The open ends of the hemispherical carrier 12 and the collimator 13 allow the treatment couch 2 to enter and exit the treatment cavity 11, thus forming an opening 111 of the treatment cavity 11. The closed ends 112 of the hemispherical source carrier 12 and collimator 13 constitute a closed end 112 of the treatment cavity 11.

As shown in FIG. 43, the gantry 1 in the embodiment of the present disclosure includes a source carrier 12 and a collimator 13, both the source carrier 12 and the collimator 13 have a hollow cylindrical structure (e.g., cone), the collimator 13 is arranged on the inner side of the source carrier 12, the inner cavity of the collimator 13 forms the treatment cavity 11 in the gantry 1, the treatment cavity 11 is used to accommodate a patient, the source carrier 12 is provided with a radiation source 121, the collimator 13 is provided with a collimating hole 131 corresponding to the radiation source 121, and the radiation emitted by the radiation source 121 passes through the collimating hole 131 to focus on a focal point O in the treatment cavity 11. One ends of the hollow cylindrical source carrier 12 and collimator 13 allow the treatment couch 2 to enter and exit the treatment cavity 11, thus forming an opening 111 of the treatment cavity 11. The other ends of the hollow cylindrical source carrier 12 and collimator 13 are blocked by a shielding plug 113, thus forming a closed end 112 of the treatment cavity 11.

As shown in FIG. 44, the outside of the source carrier 12 of the gantry according to the embodiment of the present disclosure is provided with a shielding layer 14 for surrounding the source carrier 12 to shield the radiation rays scattered from the left, right, rear, and upper sides of the radiation source apparatus 1, the shielding chamber 3 is arranged around the treatment couch 2 to house the mobile couch body 21 and the support base 22 of the treatment couch 2, and the shielding chamber 3 is coupled (directly connected or indirectly connected) with the shielding layer 14 to form a closed body for shielding the radiation rays scattered from the radiotherapy device.

According to the embodiment of the present disclosure, the closed shielding chamber is formed by the combination of the shielding chamber and the shielding layer to form self-shielding of the radiotherapy device, thereby eliminating the need for a dedicated machine room. The self-shielding radiotherapy device can be placed at any position, which expands the application scenario of the radiotherapy device.

In the embodiment of the present disclosure, the shielding chamber 3 is detachably coupled with the shielding layer 14, or the shielding chamber 3 is integrally formed with the shielding layer 14. That is: the shielding chamber 3 can be separated from the gantry 1 to serve as an accessory of the radiotherapy device, and installed according to the need of a user; or, the shielding chamber 3 can be integrally formed with the gantry 1 to serve as an inherent component of the radiotherapy device.

In the embodiment of the present disclosure, the shielding chamber is adaptively connected with the shielding layer through an adapting structure to achieve coupling.

As shown in FIG. 45, the shielding chamber 3 is adaptively connected with the shielding layer 14 through a non-straight splicing interface F, and the adapting structure is the non-straight splicing interface F. As shown in FIG. 45, the non-straight splicing interface F may be a stepped surface, or a curved surface, an S surface, a V-shaped surface, or the like. The embodiment of the present disclosure is not limited to the aforementioned non-straight splicing interface, and may also be implemented by other non-straight splicing interfaces. The non-straight splicing interface described in the embodiment of the present disclosure may realize adaptive connection by using the same interface form or different interface modes. The embodiment of the present disclosure realizes the connection between the shielding chamber and the shielding layer through the non-straight splicing interface, to ensure that no radiation leakage occurs from the interface between the shielding chamber and the shielding layer.

In the embodiment of the present disclosure, the shielding chamber is connected with the shielding layer through an intermediate connector to achieve coupling. The intermediate connector serves as a bridge connecting the shielding chamber with the shielding layer, and the shielding chamber is connected with the shielding layer through the intermediate connector.

Figure 47:
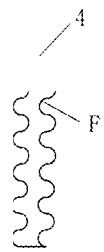
FIG. 47 is a schematic structural diagram of the intermediate connector according to an embodiment of the present disclosure.

As shown in FIG. 46, the intermediate connector 4 is adaptively connected with the shielding chamber 3 through an adapting structure; or, the intermediate connector 4 is adaptively connected with the shielding layer 14 through an adapting structure; or, the intermediate connector 4 is adaptively connected with the shielding chamber 3 and the shielding layer 14 through an adapting structure. According to the embodiment of the present disclosure, the shielding chamber 3 is connected with the shielding layer 14 through the intermediate connector 4 to overcome the mismatch between the shielding chamber 3 and the shielding layer 14 and improve the versatility of the shielding chamber. The adapting structure is a non-straight splicing interface F. As shown in FIG. 47, the non-straight splicing interface F is an S surface, or a curved surface, a stepped surface, a V-shaped surface, or the like. The embodiment of the present disclosure is not limited to the aforementioned non-straight splicing interface, and may also be implemented by other non-straight splicing interface, as long as it can ensure that no radiation leaks at the interface. The non-straight splicing interface described in the embodiment of the present disclosure may realize adaptive connection by using the same interface form or different interface modes.

Figure 48:
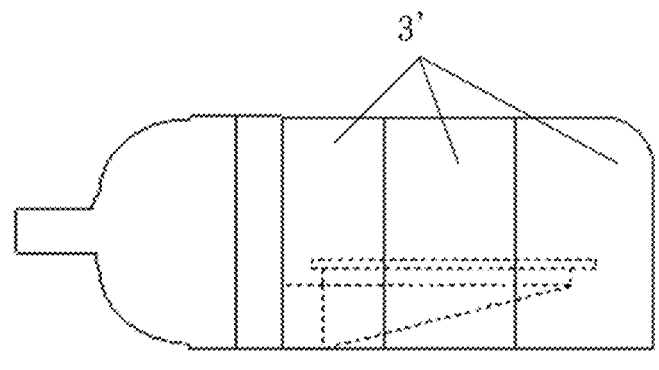
FIG. 48 is a schematic structural diagram of the shielding chamber formed by splicing shielding shell segments according to an embodiment of the present disclosure.

In an embodiment of the present disclosure, as shown in FIG. 48, the shielding chamber 3 includes a plurality of shielding shell segments 3'. According to the embodiment of the present disclosure, the shielding chamber 3 can be constituted by the plurality of shielding shell segments 3', so that the shielding chamber 3 is more convenient to transport.

In the embodiment of the present disclosure, the plurality of shielding shell segments 3' are detachably spliced o form the shielding chamber 3. According to the embodiment of the present disclosure, the plurality of shielding shell segments 3' are assembled by means of detachable splicing, so that the installation of the shielding chamber 3 is simpler, and the shielding chamber is flexibly adapted to be used in diverse places.

Figure 49A:
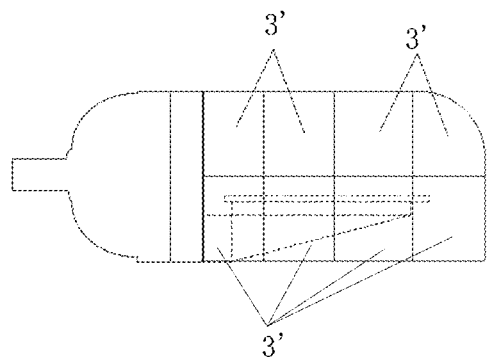
Figure 49B:
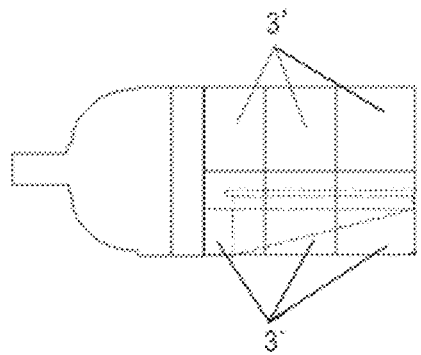
Figure 49C:
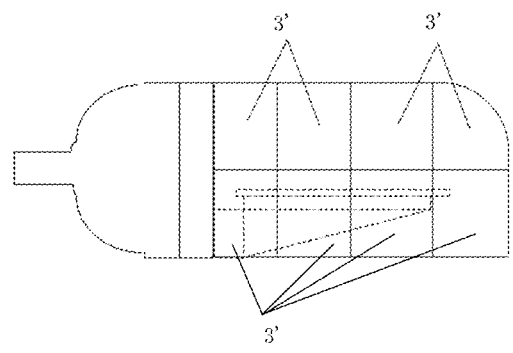
Figure 49D:
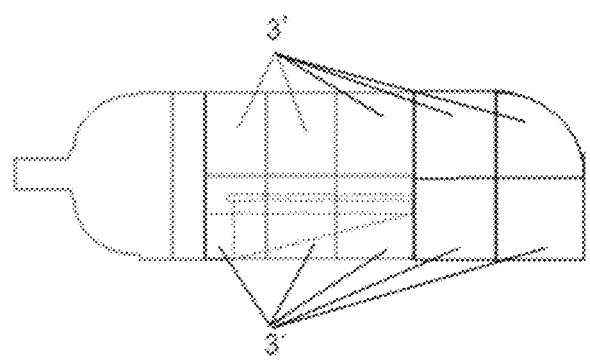

At the same time, as the plurality of shielding shell segments 3' detachably spliced are used to form the shielding chamber 3, the shape and space usage of the shielding chamber can be adjusted according to the installation place and the treatment requirements of the radiotherapy device. Referring to FIGS. 49a-49b, the embodiment of the present disclosure needs to change the shape of the shielding chamber 3, which can be achieved only by increasing or reducing the number of the shielding shell segments 3'. Referring to FIGS. 49c to 49d, the embodiment of the present disclosure needs to expand or reduce the space usage of the shielding chamber 3, which can be achieved by only increasing or reducing the number of the shielding shell segments 3'.

Referring to FIGS. 49e-49f, the embodiment of the present disclosure can also adjust the shape and space usage of the shielding chamber by increasing or reducing shielding shell segments 3' with different sizes or shapes from the original shielding shell segments 3'.

In order to prevent the radiation in the shielding chamber from leaking through the gaps between the plurality of shielding shell segments, the interfaces of the plurality of shielding shell segments are non-straight splicing interfaces.

Specifically, referring to FIG. 50, the interfaces F of the plurality of shielding shell segments 3' may be curved surfaces, or S surfaces, stepped surfaces, V-shaped surfaces, or the like.

The interfaces described in the embodiment of the present disclosure may be the same interface or different interfaces.

The embodiment of the present disclosure is not limited to the aforementioned interfaces, and may also be implemented by other non-straight splicing interfaces, as long as they can ensure that no radiation leaks at the interfaces.

The shielding chamber described in the embodiment of the present disclosure is made of metal with shielding effect, such as steel, lead, or tungsten.

In an embodiment of the present disclosure, referring to FIG. 51, the shielding chamber has at least one patient entrance 5, and the patient entrance 5 is for patients to enter and exit the shielding chamber 3.

The patient entrance 5 may be one or more, and the patient entrances 5 may be arranged on the same side or different sides of the shielding chamber 3.

The embodiment of the present disclosure is not limited to having the patient entrance 5, and a patient can also enter the shielding chamber by other means, for example, enter the shielding chamber when the splicing of the shielding shell segments has not been completed, or enter the shielding chamber through a tunnel at the location where the radiotherapy device is installed.

Specifically, the patient entrance 5 is a first openable shielding door. That is, the patient can enter and exit by opening the first openable shielding door, and the radiation is shielded by closing the first openable shielding door.

The first openable shielding door is arranged at a position of the shielding chamber 3 close to the treatment couch 2, so that the patient reaches the treatment couch 2 as soon as possible.

The first openable shielding door is arranged on a side or end of the treatment couch 2. The first openable shielding door is arranged on the side of the treatment couch 2 to facilitate the patient to get on and off the treatment couch 2. The first openable shielding door is arranged at the end of the treatment couch 2 to facilitate manual pulling of the treatment couch 2 in emergencies, so that the treatment couch 2 can quickly pass through the first openable shielding door and be dragged out of the shielding chamber.

In order to open and close the first openable shielding door, the first openable shielding door is opened electrically and/or manually.

In the embodiment of the present disclosure, the first openable shielding door may also be opened and closed by electric and manual means.

For example, the first openable shielding door is opened and closed electrically, and when a fault occurs or the radiotherapy device needs emergency operation, the first openable shielding door is manually opened.

Specifically, the first openable shielding door is one of a sliding door, a shutter door, and a side-opening door.

When there are a plurality of first openable shielding doors, different doors can be used, or the same door can be used.

According to the embodiment of the present disclosure, the form and opening and closing directions of the first openable shielding door can be selected according to the installation place and use state of the radiotherapy device.

If the radiotherapy device is installed close to the wall, a shutter door or a sliding door is selected as the first openable shielding door.

If the internal space of the radiotherapy device for installing the shielding chamber is limited, a shutter door, a sliding door, or a side-opening door opened outward is selected as the first openable shielding door.

If the first openable shielding door is a sliding door, the manual opening is achieved by manually operating a guiding or rolling structure (i.e., the first openable shielding door is manually pushed and pulled by means of the guiding or rolling structure to achieve the opening and closing of the first openable shielding door), or by hand driving (a transmission system of the first openable shielding door is driven by hand, and the first openable shielding door is further driven to achieve its opening and closing).

In order to achieve better opening and closing operations, reduce friction and increase the smoothness of opening and closing, the guiding or rolling structure is a suspended roller structure.

Referring to FIGS. 52a and 52b, the suspended roller structure includes a first top roller 51 at the top of the shielding door 5' and a first bottom slide rail 52 at the bottom of the shielding door 5', the first top roller 51 is in a first recess 33 of the shielding chamber 3, the first bottom slide rail 52 is in a second recess 34 of the shielding chamber 3 or the ground, and the shielding door 5' achieves left and right relative movement with respect to the shielding chamber 3 through the first top roller 51 and the first bottom slide rail 52 for opening and closing.

According to the embodiment of the present disclosure, the first openable shielding door is opened or closed through the first top roller 51 and the first bottom slide rail 52 at the bottom of the shielding door 5', which can realize smooth opening and closing of the first openable shielding door; and the suspended roller structure is simple to maintain and convenient to use.

Referring to FIG. 52b, the hand driving is operated through a first hand crank coupled (directly or indirectly connected) with the first openable shielding door, and the driving force generated by the hand operation is transmitted to the first openable shielding door to control the opening and closing of the first openable shielding door.

The embodiment of the present disclosure can control the opening and closing speed of the first openable shielding door by the strength and speed of the hand operation, so that when the first openable shielding door fails or the radiotherapy device fails, and an emergency operation is required to open or close the first openable shielding door, the first openable shielding door can be quickly opened and closed by the hand operation.

The embodiment of the present disclosure does not limit the installation position of the first hand crank 53, as long as the driving force generated by the hand operation can be transmitted to the first openable shielding door to control its opening and closing.

The interface between the first openable shielding door and the shielding chamber is a non-straight splicing interface.

In order to prevent the radiation in the shielding chamber from leaking through the gap between the first openable shielding door and the shielding chamber, the interface between the first openable shielding door and the shielding chamber is a non-straight splicing interface. Specifically, the interface between the first openable shielding door and the shielding chamber is one of a curved surface, an S surface, a stepped surface, and a V-shaped surface.

The interfaces described in the embodiment of the present disclosure may be the same interface or different interfaces. The embodiment of the present disclosure is not limited to the aforementioned interfaces, and may also be implemented by other non-straight splicing interfaces, as long as they can ensure that no radiation leaks at the interfaces.

Figure 53:
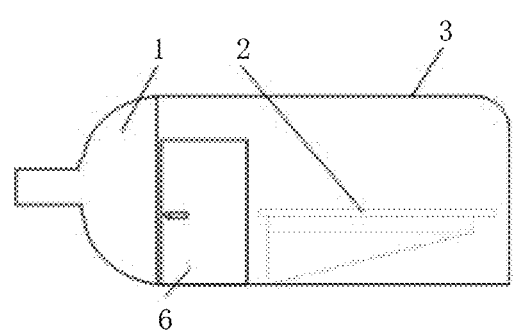
FIG. 53 is a schematic structural diagram of an operation port according to an embodiment of the present disclosure.

In an embodiment of the present disclosure, referring to FIG. 53, the shielding chamber 3 has at least one operation port 6, and the operation port 6 is for an operator to enter and exit the shielding chamber.

The operation port 6 described in the embodiment of the present disclosure may coexist in the shielding chamber 3 with the patient entrance 5, and the embodiment of the present disclosure may also have only the patient entrance 5 or only the operation port 6.

The operation port 6 is a second openable shielding door.

That is, the operator can enter and exit by opening the second openable shielding door, and the radiation is shielded by closing the second openable shielding door.

In the embodiment of the present disclosure, the second openable shielding door is arranged at a position close to the radiation source, so that the operator enters the shielding chamber to open, close or maintain the radiation source.

In order to open and close the second openable shielding door, the second openable shielding door is opened electrically and/or manually.

In the embodiment of the present disclosure, the second openable shielding door may also be opened and closed by electric and manual means.

For example, the second openable shielding door is opened and closed electrically, and when a fault occurs or the radiotherapy device needs emergency operation, the second openable shielding door is manually opened.

Specifically, the second openable shielding door is one of a sliding door, a shutter door, and a side-opening door.

When there are a plurality of second openable shielding doors, different doors can be used, or the same door can be used.

According to the embodiment of the present disclosure, the form and opening and closing directions of the second openable shielding door can be selected according to the installation place and use state of the radiotherapy device.

For example, if the radiotherapy device needs to be installed close to the wall, a shutter door or a sliding door is selected as the second openable shielding door.

For example, if the internal space of the radiotherapy device for installing the shielding chamber is limited, a shutter door, a sliding door, or a side-opening door opened outward is selected as the second openable shielding door.

Specifically, if the second openable shielding door is a sliding door, the manual opening is achieved by manually operating a guiding or rolling structure (i.e., the second openable shielding door is manually pushed and pulled by means of the guiding or rolling structure to achieve the opening and closing of the second openable shielding door), or by hand driving (a transmission system of the second openable shielding door is driven by hand, and the second openable shielding door is further driven to achieve its opening and closing).

In order to achieve better opening and closing operations, reduce friction and increase the smoothness of opening and closing, the guiding or rolling structure is a suspended roller structure.

Similar to the first openable shielding door, the suspended roller structure used by the second openable shielding door includes a second top roller at the top of the second openable shielding door and a second bottom slide rail at the bottom of the second openable shielding door, the second top roller is in a third recess of the shielding chamber, the second bottom slide rail is in a fourth recess of the shielding chamber or the ground, and the second openable shielding door achieves left and right relative movement with respect to the shielding chamber through the second top roller and the second bottom slide rail for opening and closing.

According to the embodiment of the present disclosure, the second openable shielding door is opened or closed through the second top roller and the second bottom slide rail at the bottom of the shielding door, which can realize smooth opening and closing of the second openable shielding door; and the suspended roller structure is simple to maintain and convenient to use.

The hand driving is operated by a second hand crank coupled (directly or indirectly connected) with the second openable shielding door, and the driving force generated by the hand operation is transmitted to the second openable shielding door to control the opening and closing of the second openable shielding door.

The embodiment of the present disclosure can control the opening and closing speed of the second openable shielding door by the strength and speed of the hand operation, so that when the second openable shielding door fails or the radiotherapy device fails, and an emergency operation is required to open or close the second openable shielding door, the second openable shielding door can be quickly opened and closed by the hand operation.

The embodiment of the present disclosure does not limit the installation position of the second hand crank, as long as the driving force generated by the hand operation can be transmitted to the second openable shielding door to control its opening and closing.

The interface between the second openable shielding door and the shielding chamber is a non-straight splicing interface.

In order to prevent the radiation in the shielding chamber from leaking through the gap between the second openable shielding door and the shielding chamber, the interface between the second openable shielding door and the shielding chamber is a non-straight splicing interface. Specifically, the interface between the second openable shielding door and the shielding chamber is one of a curved surface, an S surface, a stepped surface, and a V-shaped surface.

The interfaces described in the embodiment of the present disclosure may be the same interface or different interfaces. The embodiment of the present disclosure is not limited to the aforementioned interfaces, and may also be implemented by other non-straight splicing interfaces, as long as they can ensure that no radiation leaks at the interfaces.

Figure 54:
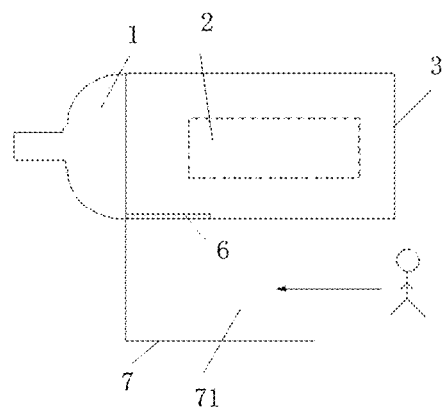
FIG. 54 is a schematic structural diagram of an isolation compartment according to an embodiment of the present disclosure.

In an embodiment of the present disclosure, in order to further avoid the leakage of radiation rays when the first openable shielding door or the second openable shielding door is opened, as shown in FIG. 54, the first openable shielding door and/or the second openable shielding door have an isolation compartment 7, and the isolation compartment 7 isolates the radiation leaked when the first openable shielding door or the second openable shielding door is opened.

In the embodiment of the present disclosure, the isolation compartment 7 isolates the radiation leaked when the first openable shielding door or the second openable shielding door is opened, thereby achieving a better radiation shielding effect.

Specifically, the isolation compartment 7 can be used for any first openable shielding door and second openable shielding door, such as one of a sliding door, a shutter door, and a side-opening door. The isolation compartment 7 can be arranged corresponding to the first openable shielding door and/or the second openable shielding door, that is, the first openable shielding door and the second openable shielding door are separately provided with the corresponding isolation compartment 7, or one isolation compartment 7 is equipped for the first openable shielding door and the second openable shielding door.

As shown in FIG. 54, the isolation compartment 7 is arranged on the outer side of the first openable shielding door and the second openable shielding door in the shielding chamber 3 to shielding the radiation leaked when the first openable shielding door or the second openable shielding door is opened, but the isolation compartment 7 is not limited to be arranged on the outer side of the first openable shielding door and the second openable shielding door, and may also be arranged at other position, for example, the inner side of the first openable shielding door and the second openable shielding door.

Referring to FIG. 54, the isolation compartment 7 includes a hollow cavity 71 arranged outside the first openable shielding door and the second openable shielding door. Before the first openable shielding door or the second openable shielding door is opened, the operator enters the hollow cavity 71 and waits for the opening of the first openable shielding door or the second openable shielding door. When the first openable shielding door or the second openable shielding door is opened, the operator quickly enters the shielding chamber 3; and when the first openable shielding door or the second openable shielding door is opened, the radiation rays leaked through the opening of the first openable shielding door or the second openable shielding door are shielded by the wall of the isolation compartment 7.

The hollow cavity 71 in the embodiment of the present disclosure may be a closed cavity or a non-closed cavity.

Figure 55:
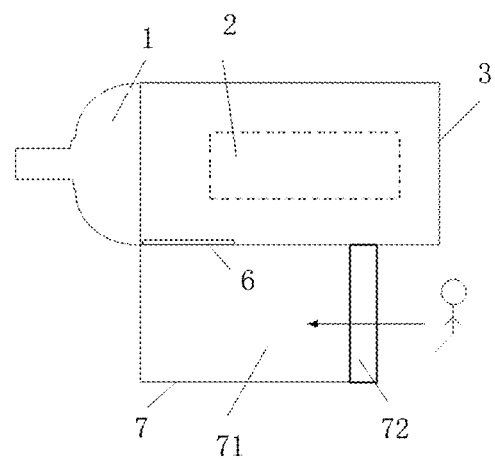
FIG. 55 is a schematic structural diagram of an isolation compartment according to an embodiment of the present disclosure.

As shown in FIG. 55, in order to further isolate the radiation leaked when the first openable shielding door or the second openable shielding door is opened, the isolation compartment 7 further includes an outer door 72 for entering the hollow cavity 71.

The outer door 72 may be one of a sliding door, a shutter door, and a side-opening door. The outer door may be one or more, or a plurality of different doors, which can isolate the radiation leaked when the first openable shielding door and the second openable shielding door are opened.

In order to open and close the outer door, the outer door is opened electrically and/or manually.

In the embodiment of the present disclosure, the outer door may also be opened and closed by electric and manual means.

For example, the outer door is opened and closed electrically, and when a fault occurs or the radiotherapy device needs emergency operation, the outer door is manually opened.

Figure 56:
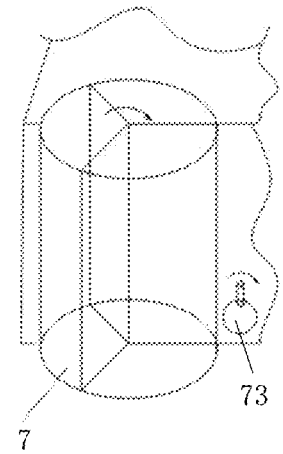
FIG. 56 is a schematic diagram of a swing gate structure according to an embodiment of the present disclosure.

Referring to FIG. 56, in an embodiment of the present disclosure, the first openable shielding door and/or the second openable shielding door are revolving doors, the revolving door has an isolation compartment 7, and the first openable shielding door and/or the second openable shielding door shield the radiation leaked when the operator enters the shielding chamber 3 through the isolation compartment 7 in the revolving door.

The revolving door is opened electrically or manually.

In the embodiment of the present disclosure, the revolving door may also be opened and closed by electric and manual means.

For example, the revolving door is revolved, opened and closed electrically, and when a fault occurs or the radiotherapy device needs emergency operation, the revolving door is manually opened.

Referring to FIG. 56, the hand driving is operated through a third hand crank 73 coupled (directly or indirectly connected) with the revolving door, and the driving force generated by the hand operation is transmitted to the revolving door to control the opening and closing of the revolving door.

The embodiment of the present disclosure can control the opening and closing speed of the revolving door by the strength and speed of the hand operation, so that when the revolving door fails or the radiotherapy device fails, and an emergency operation is required to open or close the revolving door, the revolving door can be quickly opened and closed by the hand operation.

The embodiment of the present disclosure does not limit the installation position of the third hand crank 73, as long as the driving force generated by the hand operation can be transmitted to the revolving door to control its opening and closing.

The interface between the revolving door and the shielding chamber is a non-straight splicing interface.

In order to prevent the radiation in the shielding chamber from leaking through the gap between the revolving door and the shielding chamber, the interface between the revolving door and the shielding chamber is a non-straight splicing interface. Specifically, the interface between the revolving door and the shielding chamber is one of a curved surface, an S surface, a stepped surface, and a V-shaped surface.

The interfaces described in the embodiment of the present disclosure may be the same interface or different interfaces. The embodiment of the present disclosure is not limited to the aforementioned interfaces, and may also be implemented by other non-straight splicing interfaces, as long as they can ensure that no radiation leaks at the interfaces.

In an embodiment of the present disclosure, a display and/or playback apparatus is arranged in the shielding chamber and/or the gantry, and the display and/or playback apparatus play content data according to patient preferences or user instructions.

Specifically, the patient preferences can be obtained according to patient information or selected by the patient according to user instructions, and the content data includes at least one of video content data, image content data, and sound content data. The content data played in the radiation device, for example, in the shielding chamber or the gantry, can enable the patient during the treatment to have a better visual experience, thereby alleviating the patient's claustrophobia during the treatment.

Figure 57:
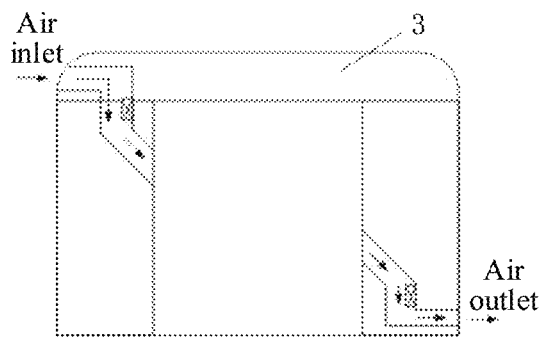
FIG. 57 is a schematic structural diagram of a fresh air system according to an embodiment of the present disclosure.

Referring to FIG. 57, in an embodiment of the present disclosure, a fresh air system is arranged in the shielding chamber 3.

An air outlet of the fresh air system is arranged at a position of the side wall of the shielding chamber close to the ground, and an air inlet is arranged at a position of the side wall of the shielding chamber close to the roof or at the top of the shielding chamber.

Specifically, the air outlet passes through the side wall along a preset oblique angle, and the air inlet passes through the side wall or the top of the shielding chamber along the preset oblique angle. The preset oblique angle is in a direction that is angled to the irradiation direction of the radiation, so as to avoid leakage of the radiation along the air outlet and/or the air inlet. Exemplarily, the preset oblique angle is 45 degrees from the horizontal direction.

A protective wall may further be arranged outside the air outlet and/or the air inlet, and the protective wall can block possible radiation leakage. The air inlet is far away from the air outlet. The distance between the air inlet and the air outlet allows air to flow in the shielding chamber, thereby supplying fresh air.

Specifically, the air inlet and the air outlet are arranged diagonally. If the distance between the air inlet and the air outlet is longer, the air flows in the shielding chamber more fully, and the ventilation effect of fresh air is better.

In the embodiment of the present disclosure, the gantry 1 of the radiation device is configured to carry a plurality of radiation sources 121, and the radiation emitted by the plurality of radiation sources 121 is focused on a point O, which is called a focal point. Generally, the focal point is on the central axis of the gantry 1.

In the embodiment of the present disclosure, the gantry rotates about its central axis. According to the embodiment of the present disclosure, continuous large-dose radiation is obtained at the lesion with fewer small-dose radiation sources through the rotation of the gantry, while surrounding normal tissues receive only a small amount of radiation, which minimizes the damage of radiotherapy.

In an embodiment of the present disclosure, the gantry 1 is used to carry a treatment head, and the treatment head is configured to emit X-rays or gamma rays. For example: the treatment head is a medical electron accelerator treatment head for emitting X-rays; the treatment head is an integrated treatment head mounted with a cobalt 60 source, for emitting gamma rays; or the treatment head is a source carrier mounted with a radiation source, i.e., a plurality of cobalt 60 sources or X-ray sources are directly mounted on the circumferential surface of the gantry for emitting gamma rays or X-rays.

In an embodiment of the present disclosure, the treatment head is configured to rotate about the central axis of the gantry, so that the treatment head emits treatment beams to the patient from various angles around the patient.

Figure 58:
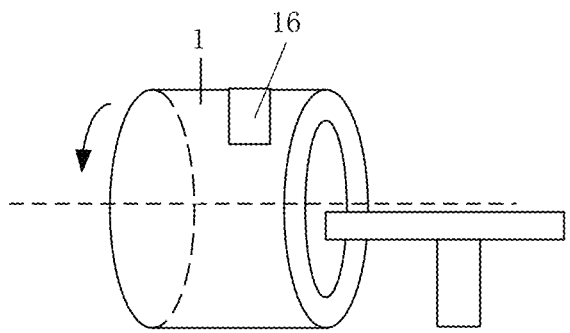
FIG. 58 is a schematic structural diagram of a radiotherapy device according to an embodiment of the present disclosure.

As shown in FIG. 58, the treatment head 16 rotates about the central axis of the gantry 1, which can be achieved by the rotation of the gantry, or by setting a rotating orbit on the gantry and driving the treatment head to move along the rotating orbit.

In an embodiment of the present disclosure, the treatment head is configured to emit X-rays or gamma rays in a direction intersecting a rotation plane, and the rotation plane is a plane perpendicular to the central axis of the gantry. According to the embodiment of the present disclosure, the treatment head can radiate the patient from multiple directions intersecting the rotation plane, and meanwhile, the treatment head can radiate the patient from multiple planes intersecting the rotation plane in combination with the rotation of the treatment head about the central axis of the gantry, to achieve near $4\pi$ radiation.

As shown in FIGS. 59 and 60, the treatment head 16 is connected to the gantry 1 via a curved guide rail 171 arranged along the axis of the gantry, the curved guide rail 171 is fixed on the gantry 1 along the axis of the gantry, the treatment head 16 is connected to the curved guide rail 171 in a sliding manner through a slider 173, the treatment head 16 is provided with a curved rack 172 extending along the axis of the gantry, the gantry 1 is provided with a driving apparatus 181, and an output end of the driving apparatus 181 is connected with a gear 182 meshing with the curved rack 172. The gear 182 transmits the driving force of the driving apparatus 181 to the treatment head 16, to drive the treatment head 16 to move along the curved guide rail 171, so that the treatment head 16 radiates the patient from multiple directions intersecting the rotation plane.

The treatment head is connected to the gantry through a pivot, and the treatment head radiates the patient from multiple directions intersecting the rotation plane through the rotation of the pivot.

In an embodiment of the present disclosure, an image system is arranged in the shielding chamber and/or in the gantry. The image system includes an X-ray generator and a detector arranged oppositely, and rays emitted by the X-ray generator pass through the body of the patient and are received by the detector to image lesions and/or organs in the body of the patient.

The image system may be arranged in the shielding chamber, or in the gantry, or in both the shielding chamber and the gantry. The radiotherapy device according to the embodiment of the present disclosure may be equipped with one or more sets of the aforementioned image systems. The embodiment of the present disclosure does not limit the number of the image systems in the radiotherapy device.

In an embodiment of the present disclosure, a slip ring is arranged on the gantry for power transmission and/or signal transmission carried out up and down the gantry. The slip ring includes a stator and a rotor; the rotor is coaxially connected with an end face of the cylindrical gantry, and is rotatable with the cylindrical gantry; the stator is fixed on the gantry, and the stator is connected to a power source and/or a signal source. The coupling between the stator and the rotor provides power transmission and/or signal transmission for the rotating gantry.

In another embodiment of the present disclosure, the gantry of the radiation device is specifically a radiation source apparatus 1, a treatment cavity 11 is formed in the radiation source apparatus 1, one end of the radiation source apparatus 1 has an opening 111 for the treatment couch 2 to enter and exit the treatment cavity, and the end of the treatment cavity 11 opposite to the opening 111 is a closed end 112.

The radiation source 121 mounted on the source carrier 12 of the radiation source apparatus 1 is an X-ray source or a gamma ray source. For example: a medical electron accelerator for emitting X-rays; a cobalt 60 source for emitting gamma rays.

In an embodiment of the present disclosure, the radiation source 121 mounted on the source carrier 12 of the radiation source apparatus 1 is an X-ray source or a gamma ray source. For example: a medical electron accelerator for emitting X-rays; a cobalt 60 source for emitting gamma rays.

In an embodiment of the present disclosure, the source carrier 12 of the radiation source apparatus 1 is mounted with a plurality of radiation sources 121, and rays emitted by the plurality of radiation sources 121 are focused on a point O, which is called a focal point. Generally, the focal point is on the central axis of the radiation source apparatus 1.

In an embodiment of the present disclosure, as shown in FIG. 61, the plurality of radiation sources 121 include a plurality of radiation source groups 1211. As shown in FIG. 61, the plurality of radiation sources 121 includes six radiation source groups 1211. The plurality of radiation source groups 1211 are uniformly distributed on the entire circumferential surface of the source carrier 12 of the radiation source apparatus, and the radiation sources 121 in each radiation source group 1211 are distributed in different latitude areas of the source carrier 12 of the radiation source apparatus, to implement focused radiation on the patient from different directions.

In the embodiment of the present disclosure, as shown in FIG. 62, the plurality of radiation sources 121 include a plurality of radiation source groups 1211, the plurality of radiation source groups 1211 are concentrated in an area Q of the circumferential surface of the source carrier 12 of the radiation source apparatus, and the radiation sources 121 in each radiation source group 1211 are distributed in different latitude areas of the source carrier 12 of the radiation source apparatus, to implement focused radiation on the patient from different directions.

In an embodiment of the present disclosure, the radiation source apparatus rotates about its central axis 1. According to the embodiment of the present disclosure, continuous large-dose radiation is obtained at the lesion with fewer small-dose radiation sources through the rotation of the radiation source apparatus, while surrounding normal tissues receive only a small amount of radiation, which minimizes the damage of radiotherapy.

In an embodiment of the present disclosure, an image system is arranged in the shielding chamber and/or in the radiation source apparatus. The image system includes an X-ray generator and a detector arranged oppositely, and rays emitted by the X-ray generator pass through the body of the patient and are received by the detector to image lesions and/or organs in the body of the patient.

The image system may be arranged in the shielding chamber, or in the radiation source apparatus, or in both the shielding chamber and the radiation source apparatus. The radiotherapy device according to the embodiment of the present disclosure may be equipped with one or more sets of the aforementioned image systems. The embodiment of the present disclosure does not limit the number of the image systems in the radiotherapy device.

In an embodiment of the present disclosure, the radiotherapy device further includes an optical monitoring system, the optical monitoring system can be used to monitor the movement of the patient on the treatment couch, and the optical monitoring system may be an infrared monitoring system.

The optical monitoring system may include a ray generator, a ray receiver and a marker. When in use, the marker is attached to the surface of the patient's body, rays emitted by the ray generator are reflected by the marker and received by the ray receiver, and the movement of the patient is determined by the time of receiving the reflected rays.

The optical monitoring system may further include a ray receiver and a marker. When in use, the marker is attached to the surface of the patient's body, the marker automatically emits rays, the rays are received by the ray receiver, and the movement of the patient is determined by the time of receiving the rays.

The optical monitoring system may further include a ray transmitter and a ray receiver. When in use, rays emitted by the ray generator are reflected by the patient's skin and received by the ray receiver, and the movement of the patient is determined by the time of receiving the reflected rays.

The optical monitoring system may further include only a ray receiver. When in use, the patient's skin reflects natural light, the reflected natural light is received by the ray receiver, and the movement of the patient is determined by the time of receiving the reflected natural light.

The optical monitoring system is arranged on the treatment couch. As shown in FIG. 63, the optical monitoring system 8 is arranged at the tail of the treatment couch 2. The optical monitoring system may also be arranged at other position of the radiotherapy device, for example, arranged at the upper part of the treatment couch, or suspended at the top of the shielding chamber.

In the present disclosure, the treatment couch may be a three-dimensional couch, that is, the treatment couch is movable in the transverse, longitudinal, and lifting directions. Of course, the treatment couch may also be a four-dimensional, five-dimensional or six-dimensional couch, which means to increase the rotation or swing of the treatment couch in the transverse and/or longitudinal and/or lifting directions based on the aforementioned three-dimensional couch.

In the present disclosure, the shielding chamber may be directly fixedly connected to the ground, or fixedly connected to the base of the radiotherapy device.

In the present disclosure, the shielding chamber may be fixedly connected to the ground or the base of the radiotherapy device by anchor bolts, the shielding chamber may be fixedly connected to the shielding layer by bolts, and the shielding shell segments of the shielding chamber may be fixedly connected by bolts. Of course, the fixed connection may also be achieved by other means, for example, by welding, bonding, screw-nut connection, etc. The present disclosure does not limit the means of fixed connection.

The present disclosure further provides a radiotherapy device, including the shielding apparatus described in any one of the above. Specifically, the radiotherapy device is an accelerator or gamma knife radiotherapy device.

Finally, it should be noted that the above embodiments are merely intended to describe the technical solutions according to the embodiments of the present disclosure, instead of limiting the present disclosure. Although the present disclosure is described in detail with reference to the above embodiments, persons of ordinary skill in the art should understand that various modifications may be made to the technical solutions described in the above embodiments or equivalent replacements may be made to some technical features thereof, without departing from the spirit and scope of the technical solutions of the embodiments of the present disclosure.

What is claimed is:

1. A radiotherapy device, the radiotherapy device comprising:
at least one shielding shell segment, the at least one shielding shell segment constituting a shielding chamber;
a gantry configured to carry a radiation source for emitting X-rays or gamma rays; and wherein the shielding chamber is arranged on a periphery of the radiotherapy device; and
a shielding layer arranged on an outside of the gantry with the gantry being enclosed by the shielding layer, wherein the shielding layer is at least partially exposed outside of the shielding chamber and connected with the shielding chamber, and X-rays or gamma rays generated by the radiotherapy device are shielded by a combination of the shielding chamber and the shielding layer;

wherein the shielding chamber includes at least one entrance, the entrance is a third openable shielding door, the third openable shielding door is arranged at a position of the shielding chamber opposite to the shielding layer, and an opening size of the third openable shielding door is smaller than a size of the shielding layer in an axial direction of the radiotherapy device.

2. The radiotherapy device according to claim 1, wherein the radiotherapy device comprises a treatment couch, the treatment couch comprises a mobile couch body and a support base, and the shielding chamber surrounds the mobile couch body and the support base.

3. The radiotherapy device according to claim 1, wherein the shielding chamber is detachably connected with the shielding layer, or the shielding chamber is integrally formed with the shielding layer.

4. The radiotherapy device according to claim 3, wherein the shielding chamber is adaptively connected with the shielding layer through an adapting structure.

5. The radiotherapy device according to claim 4, wherein the adapting structure is a non-straight splicing interface.

6. The radiotherapy device according to claim 3, wherein the shielding chamber is connected with the shielding layer through an intermediate connector.

7. The radiotherapy device according to claim 6, wherein the intermediate connector is adaptively connected with at least one of the shielding chamber and the shielding layer through an adapting structure.

8. The radiotherapy device according to claim 7, wherein the adapting structure is a non-straight splicing interface.

9. The radiotherapy device according to claim 1, wherein the at least one shielding shell segment is plural in number and the plurality of shielding shell segments are detachably spliced to form the shielding chamber.

10. The radiotherapy device according to claim 1, wherein the shielding chamber includes at least one patient entrance for a patient to enter and exit the shielding chamber.

11. The radiotherapy device according to claim 10, wherein the patient entrance is a first openable shielding door.

12. The radiotherapy device according to claim 11, wherein the shielding chamber includes an isolation compartment, and the isolation compartment is used to isolate the radiation leaked when the first openable shielding door is opened.

13. The radiotherapy device according to claim 1, wherein the shielding chamber includes at least one operation port for an operator to enter and exit the shielding chamber.

14. The radiotherapy device according to claim 13, wherein the operation port is a second openable shielding door.

15. The radiotherapy device according to claim 14, wherein the shielding chamber includes an isolation compartment, and the isolation compartment is used to isolate the radiation leaked when the shielded door is opened.

16. The radiotherapy device according to claim 1, the shielding chamber includes a first shielding chamber and a second shielding chamber that are arranged on sides of the gantry in an axis direction of the gantry and connected with the shielding layer to form a closed body.

17. The radiotherapy device according to claim 1, wherein the shielding layer covers an outside surface of the gantry in an axis direction of the gantry to shield X-rays or gamma rays scattered from left, right and upper sides of the gantry.

* * * * *